US006923063B2

(12) United States Patent
Komninos

(10) Patent No.: US 6,923,063 B2
(45) Date of Patent: Aug. 2, 2005

(54) ACOUSTIC SENSING DEVICE, SYSTEM AND METHOD FOR MONITORING EMISSIONS FROM MACHINERY

(75) Inventor: Nikolaos I. Komninos, Littleton, CO (US)

(73) Assignee: Radiaulics, Inc., Littleton, CO (US)

( * ) Notice: Subject to any disclaimer, the term of this patent is extended or adjusted under 35 U.S.C. 154(b) by 0 days.

(21) Appl. No.: 10/245,796

(22) Filed: Sep. 16, 2002

(65) Prior Publication Data

US 2004/0050163 A1 Mar. 18, 2004

(51) Int. Cl.[7] .............................................. G01N 29/04
(52) U.S. Cl. ............................ 73/587; 73/593; 73/660
(58) Field of Search .................... 73/587, 593, 649, 73/652, 658, 660, 116, 117.2, 117.3, 659

(56) References Cited

U.S. PATENT DOCUMENTS

| | | | | |
|---|---|---|---|---|
| 3,308,647 A | * | 3/1967 | Crawford | 73/1.84 |
| 3,375,707 A | * | 4/1968 | Neitz | 73/658 |
| 3,555,894 A | * | 1/1971 | Bratkowski | 340/870.39 |
| 4,011,472 A | * | 3/1977 | Feng | 310/8.1 |
| 4,612,620 A | * | 9/1986 | Davis et al. | 702/184 |
| 4,922,754 A | * | 5/1990 | Horne et al. | 73/587 |
| 5,452,264 A | * | 9/1995 | Holroyd | 367/140 |
| 5,546,809 A | * | 8/1996 | Cotton | 73/644 |
| 5,631,426 A | * | 5/1997 | Jao | 73/644 |
| 5,691,707 A | | 11/1997 | Smith et al. | |
| 5,845,230 A | * | 12/1998 | Lamberson | 702/56 |
| 5,992,237 A | * | 11/1999 | McCarty | 73/659 |
| 6,053,047 A | * | 4/2000 | Dister et al. | 73/593 |
| 6,205,872 B1 | * | 3/2001 | Pflueg | 73/866.5 |
| 6,289,735 B1 | * | 9/2001 | Dister et al. | 73/579 |
| 6,321,602 B1 | * | 11/2001 | Ben-Romdhane | 73/660 |
| 6,598,479 B1 | * | 7/2003 | Robinson et al. | 73/658 |

FOREIGN PATENT DOCUMENTS

| | | | | |
|---|---|---|---|---|
| JP | 62159041 A | * | 7/1987 | G01N/29/04 |
| WO | WO 98/01831 | * | 1/1998 | G07C/3/00 |

* cited by examiner

*Primary Examiner*—Hezron Williams
*Assistant Examiner*—Rose M. Miller
(74) *Attorney, Agent, or Firm*—Timothy J. Martin; Michael R. Henson; Rebecca A. Gegick

(57) ABSTRACT

A device and system are provided for monitoring acoustic emissions from machinery to indicate levels of detected sound waves. Each incorporates an acoustic sensing device which incorporates a housing assembly constructed for removable attachment between a surface mounting region of the machinery and a measuring instrument to define a coupled state. An acoustic emissions sensor is disposed in the housing assembly's interior to detect sound waves propagating through the surface mounting region and to produce detection signals for processing by the measuring instrument. A methodology for monitoring acoustic emissions is also provided.

16 Claims, 16 Drawing Sheets

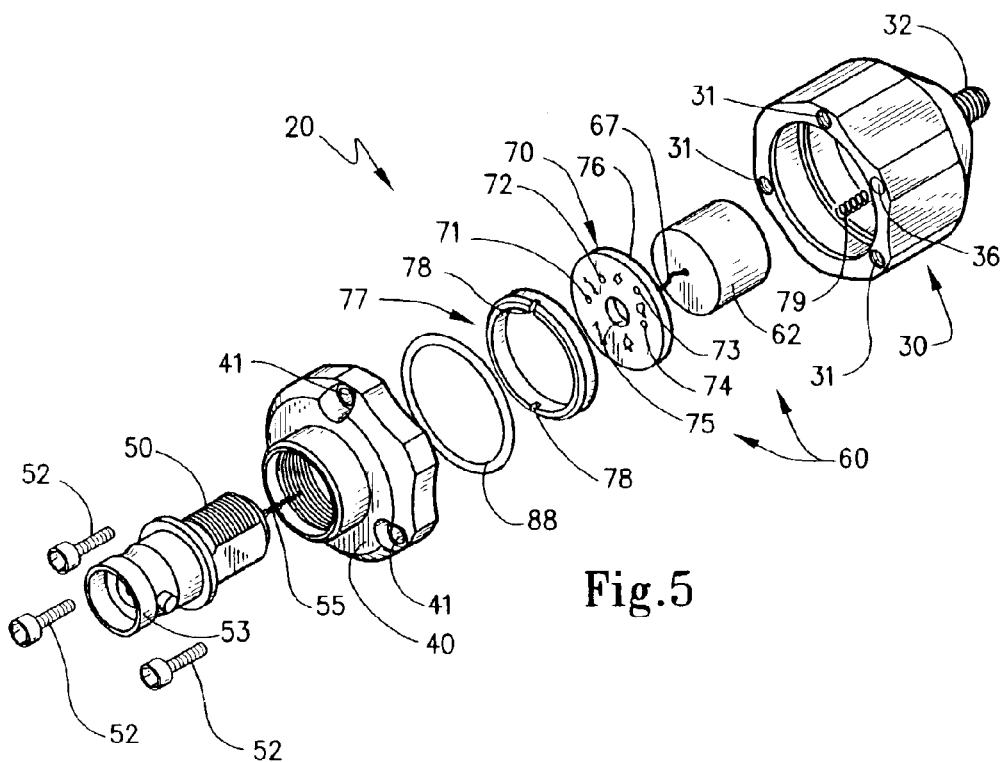
Fig.5
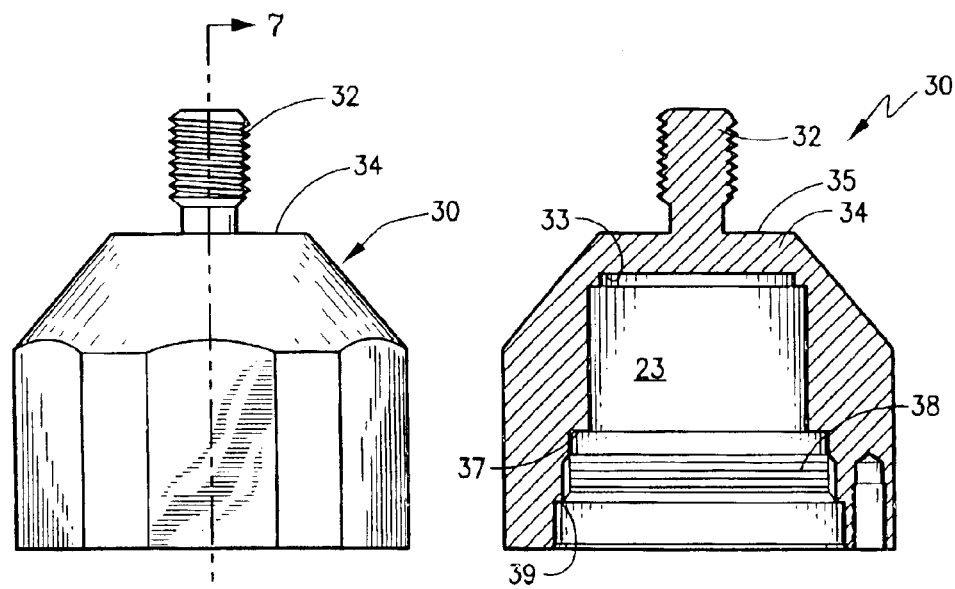
Fig.6
Fig.7

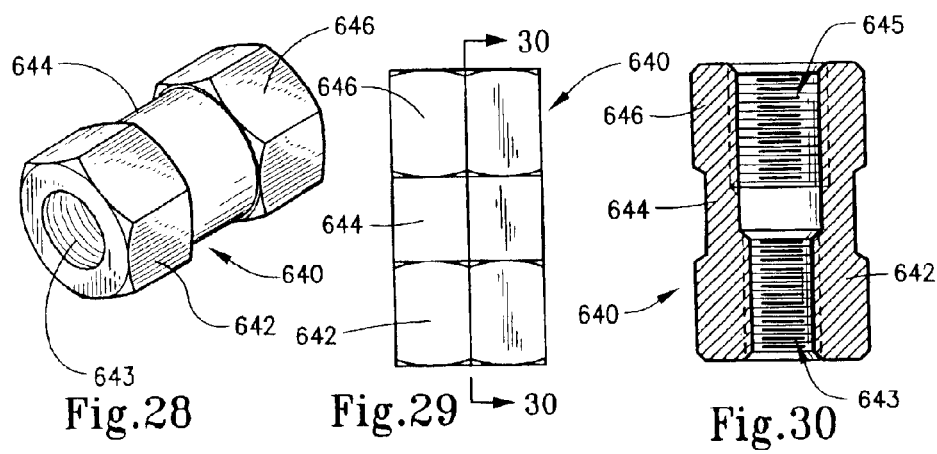
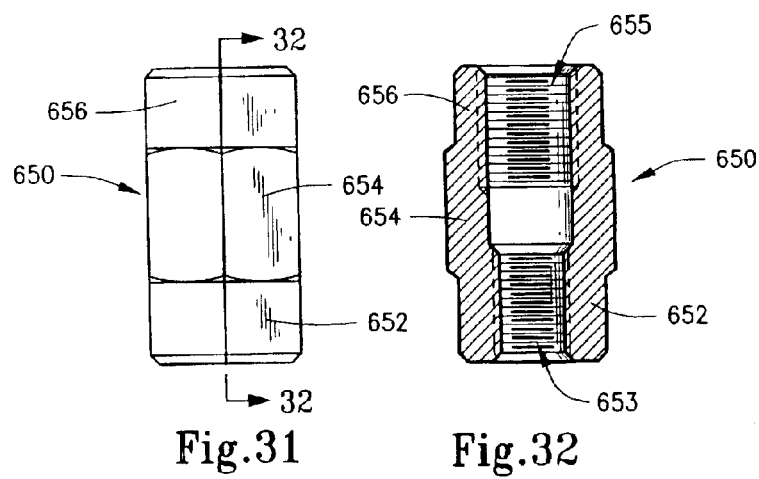
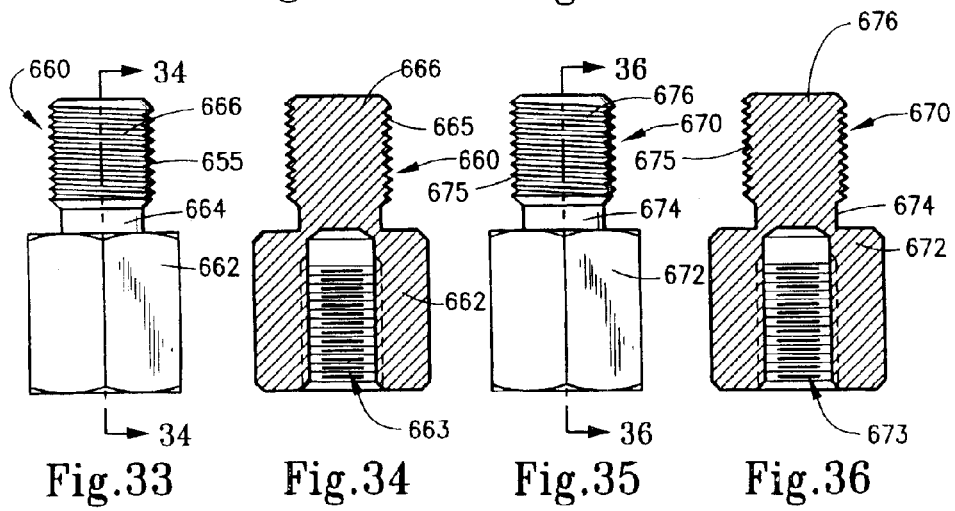

ACOUSTIC SENSING DEVICE, SYSTEM AND METHOD FOR MONITORING EMISSIONS FROM MACHINERY

FIELD OF THE INVENTION

The present invention broadly relates to the field of machinery diagnostics and, more particularly, concerns the monitoring of acoustic emissions from machinery or components thereof. The present invention is even more specifically directed to sensing devices, systems and methodologies for measuring acoustic emissions.

BACKGROUND OF THE INVENTION

There are many situations in which it is both desirable and important to monitor the operability of machinery or other equipment components. Diagnostically assessing the operability of machinery can establish the running condition of the machinery in a fashion which is objective and scientific. For example, routine diagnostic procedures adopted by maintenance personal can help detect early signs of machinery malfunction or failure and, thus, lead to corrective and preventive measures to ensure machinery is functioning within desired operational parameters. Instances where such procedures can prove useful include the detection of early bearing failure, internal/external fluid leakage, cavitation in hydraulic systems, steam trap leakage, gear problems, bearing lubrication status, as well as a multitude of other machine diagnostic functions.

Predictive mechanical maintenance through vibration measurement of machinery illustrates one common approach to diagnosing and preventing machinery malfunctions, and it is known to employ different types of industrial vibration sensors, such as accelerometers, in conjunction with measuring instrumentation to help pinpoint and ultimately rectify mechanical deficiencies. A full range of accelerometers are available in the marketplace to meet unique applications. Accelerometers generally incorporate internal seismic masses which measure the acceleration of internal forces generated by internal moving parts, and they can be removably or permanently attached to surface mounting regions of machinery and coupled to measuring instrumentation, such as a vibration analyzer, to measure the motion of internal machine parts.

Another approach to diagnosing machinery and other types of mechanical systems is by using sensors which actually "listen" to structures and materials to detect acoustic emissions activity. Pressure vessels, storage tanks, heat exchangers, piping, reactors, aerial lift devices, nuclear power plants, and refrigeration systems illustrate some common examples in which acoustic emissions activity can be monitored. While acoustic emissions sensors, like accelerometers, are available in a wide variety of configurations and for a wide variety of particular applications, one particular application is the use of acoustic emission sensors in ultrasonic signal detectors to assess the existence of internal or external leaks associated with a system. Various types of ultrasonic leak detectors are disclosed in my following patents: U.S. Pat. No. 5,103,675 issued Apr. 14, 1992, U.S. Pat. No. 5,432,755 issued Jul. 11, 1995, U.S. Pat. No. 5,436,556 issued Jul. 25, 1995, U.S. Pat. No. 6,058,076 issued May 2, 2000, U.S. Pat. No. 6,079,275 issued Jun. 27, 2000, U.S. Pat. No. 6,128,959 issued Oct. 10, 2000, and U.S. Pat. No. 6,163,504 issued Dec. 19, 2000.

It has heretofore, however, been unknown to utilize an acoustic emission sensor in conjunction with measuring instrumentation, similar to the manner in which accelerometers have been employed, for the purpose of measuring sound internal to machinery or systems. By employing acoustic emission sensors which can be either permanently or removably mounted to appropriate surface regions of machinery, one can obtain useful information about the sound characteristics of the machinery which can facilitate calibration, maintenance and diagnostics. If desired, this approach can be used in conjunction with other known diagnostic and monitoring techniques as part of a routine maintenance schedule. The present invention is directed to meeting these needs, among others.

SUMMARY OF THE INVENTION

It is an object of the present invention to provide an acoustic sensing device for use in transmitting to a measuring instrument sound wave levels detected from machinery.

Another object of the present invention is to provide a new and improved system for monitoring acoustic emissions from machinery.

A further object of the present invention is to provide a new and improved methodology for monitoring acoustic emissions from machinery.

Still another object of the present invention is to provide such an acoustic sensing device, system and methodology which allows measurement information to be retrieved during separate reading intervals to establish a running condition of machinery during its life cycle.

Still a further object of the present invention is to provide such an acoustic sensing device, system and methodology which permits one or more remote sensors to be selectively and removably attached to machinery, or different portions thereof, and monitored at one's convenience.

In accordance with these objectives, the present invention provides an acoustic sensing device for use in transmitting to a measuring instrument detection signals indicative of sound wave levels detected from machinery, with the acoustic sensing device broadly comprising a housing assembly and an acoustic emissions sensor disposed in an interior of the housing assembly. For purposes of the disclosure herein, the term "machinery" encompasses any of a variety of types of equipment or components thereof, the performance of which it is desirable to monitor or diagnose. Accordingly, the term should be interpreted as broadly as possible in conformity with the objectives of the present invention.

The housing assembly for the acoustic sensing device is preferably constructed for removable attachment between a surface mounting region of the machinery and the measuring instrument to define a coupled state. The acoustic emissions sensor which is disposed within the housing assembly is operative when the housing assembly is in the coupled state to detect sound waves propagating through the surface mounting region and produce the detection signals which can then be processed by the measuring instrument.

A coupler, such as a coaxial connector, a multi-pin connector, or a MIL type connector, is used to interface the housing assembly with the measuring instrument via an appropriate communications interface. Alternatively, the coupler may form part of the housing assembly. In one embodiment for the acoustic sensing device, the housing assembly includes a housing body constructed to directly couple to the surface mounting region of the machinery. In another embodiment of the acoustic sensing device, a mounting adapter is included for indirectly coupling the housing assembly to the surface mounting region. To this end, the mounting adapter releasably attaches to the surface mounting region of the machinery and the housing body releasably attaches to the mounting adapter.

While a variety of mounting capabilities are contemplated, preferred embodiments of the present invention provide for threaded engagement between the housing assembly and the mounting adapter, as well as either threaded, magnetic, or adhesive coupling between the mounting adapter and the surface mounting region of the machinery. More particularly, the housing body may include a mount disposed on a first end portion thereof to permit removable attachment of the housing body relative to the machinery either directly or indirectly through the mounting adapter. This mount may be formed integrally with the housing body and have a threaded male projection of a selected thread size which extends from the first end portion. This threaded projection is matably received within a correspondingly sized threaded bore formed in either the machinery or the mounting adapter. Where the mounting adapter is employed, it may have a second threaded bore for threadedly engaging a correspondingly sized threaded projection extending from the surface mounting region of the machinery. Alternatively, the mounting adapter may have its own threaded projection for engaging a corresponding threaded bore formed in the machinery. In yet another configuration, the mounting adapter has a first threaded bore for receiving the mount from the housing body and at least one magnetic element for magnetically coupling to the surface mounting region.

The acoustic emissions sensor preferably includes a piezoelectric transducer adapted upon exposure to the sound waves propagating through the surface mounting region of the machinery to mechanically stress and produce corresponding transducer signals. Conditioning circuitry is employed for receiving these transducer signals and producing the detection signals for processing by the measuring instrument. The first end portion of the housing is preferably formed with a substantially planar wall having substantially planar inner and outer contact surfaces. The outer contact surface is oriented in a facing relationship to the surface mounting region of the machinery when the housing body is removably attached relative thereto. The piezoelectric transducer has a mounting face immovably secured to the inner contact surface of the planar end wall. The transducer extends longitudinally within the housing interior from this mounting face to terminate in an unrestrained free end portion so that the transducer may stress longitudinally when exposed to the sound waves and produce the corresponding transducer signals. The conditioning circuitry is preferably contained on a common circuit board that is disposed within the housing interior and immovably supported therein by a retainer. This conditioning circuitry is grounded to the housing assembly which itself is electrically conductive.

In an exemplary embodiment of the acoustic sensing device of the present invention, the housing body includes a main body section, which is formed to include the mount, and an end cap which is secured to the main body section by a plurality of fastening elements. Both the main body section and the end cap may be formed from an electrically conductive material, such as stainless steel or aluminum. Preferably, however, these housing body pieces are anodized aluminum and there is an electrically conductive compression spring interposed between spot faced portions of them to establish electrical conductivity and provide adequate shielding.

A system is also provided for monitoring acoustic emissions from machinery. Here, the system broadly comprises at least a first acoustic sensing device as discussed above and measuring instrumentation coupled to the device's acoustic emissions sensor via a first communications interface. This measuring instrumentation is operative upon receipt of detection signals from the acoustic emission sensor to display perceptible output indicative of the detected sound wave levels. A vibration analyzer may be provided having an internal power supply for activating the acoustic emission sensor and the conditioning circuitry. Alternatively, the measuring instrumentation may be in the form of a spectrum analyzer, while an auxiliary handheld unit houses both the conditioning circuitry and an auxiliary power supply. Here, the acoustic sensing device is coupled to the spectrum analyzer through the auxiliary handheld unit.

In an alternative embodiment of the system, a second acoustic sensing device is provided and removably attached relative to an associated second surface mounting region of the machinery. This second acoustic sensing device may have an associated second acoustic emissions sensor coupled to the measuring instrumentation via a second communications interface. A switch is included and operative in a first switch condition to interconnect an input of the measuring instrumentation to an output of the first acoustic sensing device and operative in a second switch condition to interconnect the input of the measuring instrumentation to an output of the second acoustic sensing device.

The present invention also relates to a method for monitoring acoustic emissions from machinery. A first embodiment of this methodology relates to a single acoustic sensing device and comprises the steps of mounting the acoustic sensing device relative to a surface mounting region of the machinery thereby to expose the device for a selected exposure period to sound waves propagating through the surface. The methodology also contemplates coupling the acoustic sensing device to a measuring instrument along a communications interface and transmitting an initial set of detection signals from the acoustic sensing device to the measuring instrument along the communication's interface, whereby the initial set of detection signals corresponds to sound wave levels propagating through the surface which are detected by the acoustic sensing device during an initial reading interval. Thereafter, the measuring instrument may display perceptible output correlated to the initial set of detection signals received from the acoustic sensing device during the initial reading interval.

The methodology may also provide for decoupling the acoustic sensing device from the measuring instrument for a selected time interval and thereafter re-coupling the acoustic sensing device and transmitting a subsequent set of detection signals to the measuring instrument corresponding to sound wave levels propagating through the machinery surface during a subsequent reading interval. Perceptible output is then displayed on the measuring instrument correlated to the subsequent set of detection signals which may then be compared with the initial set of detection signals.

In a second embodiment of the methodology, a plurality of sensing devices are mounted to respective surface mounting regions of the machinery, with at least one of the sensing devices being an acoustic sensing device as discussed above. The sensing devices are selectively interfaced with the measuring instrumentation and corresponding sets of readings are selectively received from each of the sensing devices during a plurality of associated reading intervals. Perceptible output is then displayed on the measuring instrumentation corresponding to the associated sets of readings received by the measuring instrumentation from each of the sensing devices.

These and other objects of the present invention will become more readily appreciated and understood from a consideration of the following detailed description of the exemplary embodiments when taken together with the accompanying drawings, in which:

BRIEF DESCRIPTION OF THE DRAWINGS

FIG. 5 is an exploded perspective view of the acoustic sensing device of FIGS. 2–4;

FIG. 6 is a side view in elevation of the acoustic sensing device's main body portion;

FIG. 7 is a cross-sectional view of the main body portion as seen about line 7—7 in FIG. 6;

FIG. 28 is a perspective view of a second exemplary embodiment of a mounting adapter which may be used with any of the acoustic sensing devices of the present invention;

FIG. 29 is a side view in elevation of the mounting adapter shown in FIG. 28;

FIG. 30 is a cross-sectional view of the mounting adapter as seen about lines 30—30 in FIG. 29;

FIG. 31 is a side view in elevation of a third exemplary embodiment for a mounting adapter which may be used with the acoustic sensing devices of the present invention;

FIG. 32 is a cross-sectional view of the mounting adapter as seen about lines 32—32 in FIG. 31;

FIG. 33 is a fourth exemplary embodiment for a mounting adapter which may be used with the acoustic sensing devices of the present invention;

FIG. 34 is a cross-sectional view of the mounting adapter as seen about lines 34—34 in FIG. 33;

FIG. 35 is a fifth exemplary embodiment of a mounting adapter which may be used with the acoustic sensing devices of the present invention;

FIG. 36 is a cross-sectional view of the mounting adapter as seen about lines 36—36 in FIG. 35;

DETAILED DESCRIPTION OF THE EXEMPLARY EMBODIMENTS

The present invention relates to acoustic sensing devices, systems and methodologies for monitoring acoustic emissions from machinery. The invention in its various forms can be used to help maintenance personnel detect early bearing failure, internal/external fluid leakage, cavitation in hydraulic systems, steam trap leakage, gear problems, bearing lubrication status, as well as a multitude of other machine diagnostic functions.

Figure 1:
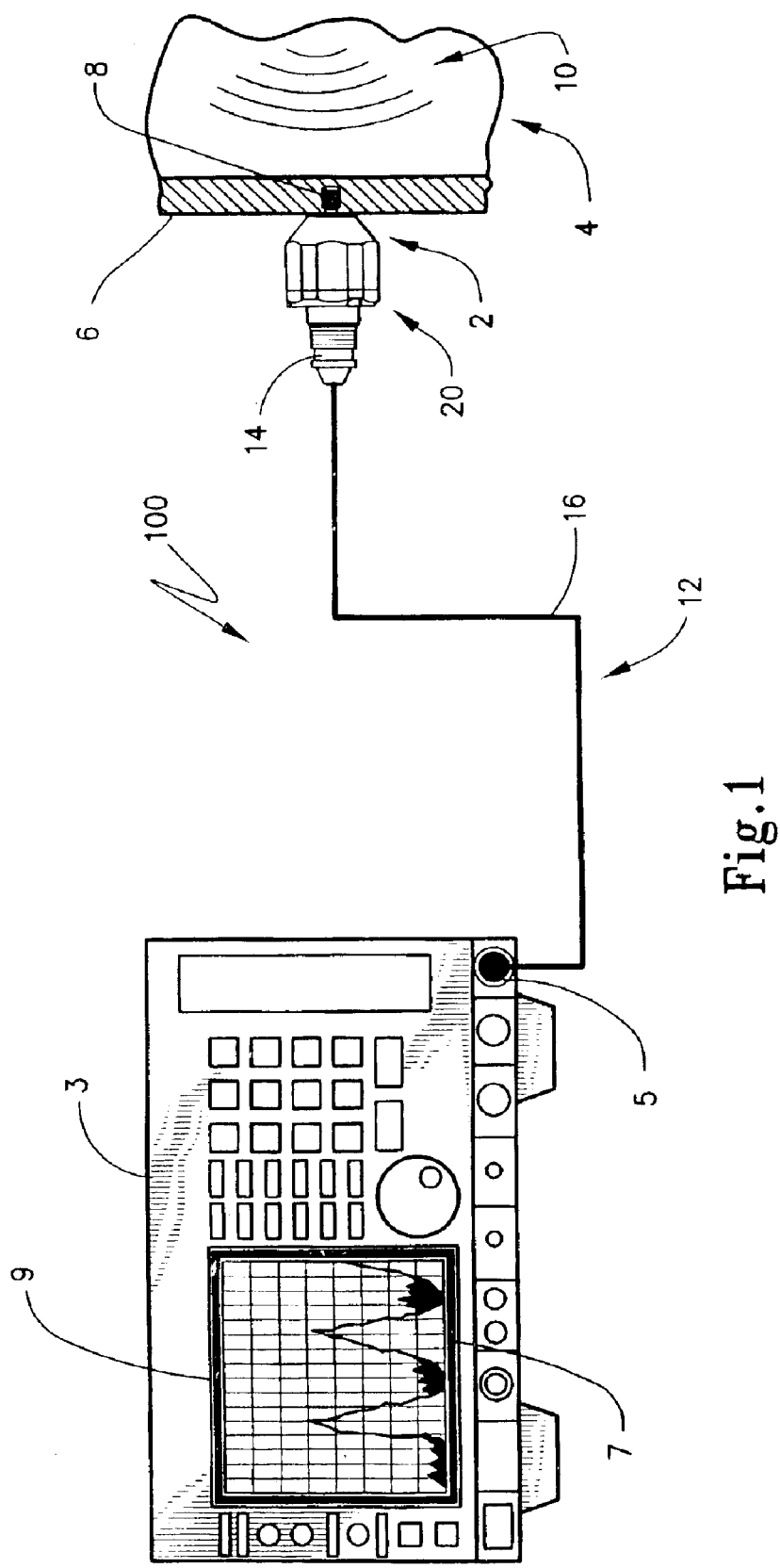
FIG. 1 is a diagrammatic view of a first exemplary embodiment of a system for monitoring acoustic emissions from machinery.

A first exemplary embodiment of a system for monitoring acoustic emissions from machinery is diagrammatically illustrated in FIG. 1. System 100 comprises an acoustic sensing device 20 that is attached to a surface mounting region 2 of a piece of equipment 4, or a component thereof, which acoustic sensing device 20 is operative upon activation to detect a presence of sound waves 8 which propagate through surface mounting region 2. As stated above, machinery 14 can be any type of equipment or component thereof from which it is desirable to monitor internal acoustic emissions. Although not necessary, it is preferred that acoustic sensing device 20 be removably mounted to surface mounting region 2. As shown in FIG. 1, for example, surface mounting region 2 includes a wall portion 6 of machinery 4 provided with a threaded bore 8 which is threadedly engaged by acoustic sensing device 20 in a direct coupled arrangement. To this end, the acoustic sensing device is conveniently adapted for use with a variety of different types of machinery, such as machinery 4, that are manufactured to include access locations, such as threaded bore 8 which accommodate the removable attachment of other types of sensors known as accelerometers. Accordingly, the present invention has been adapted to provide an acoustic sensing device which can likewise be selectively and removably attached to the same access locations on machinery. Of course, the ordinarily skilled artisan should readily appreciate from the description herein that certain embodiments of the acoustic sensing device can be attached at virtually any surface mounting region of a piece of equipment whether or not it is initially manufactured to include a threaded bore, such as bore 8, or other type of known sensor accessible location.

System 100 also incorporates measuring instrumentation 3, illustrated in the embodiment of FIG. 1 as a conventional vibration analyzer, to which acoustic sensing device 20 is coupled via an appropriate communications interface 12. Communications interface 12 is shown in the embodiment of FIG. 1 to be in the form of a conventional coaxial cable coupling acoustic sensing device 20 to measuring instrumentation 3, although the ordinarily skilled artisan would readily appreciate that various other types of known interfacing techniques, for example, an MIL Type or any other shielded cable/connector combination could be employed to establish continuity between sensing device 20 and measuring instrumentation 3. In FIG. 1, interface 12 specifically includes a pair of coaxial connectors 5 and 14, such as BNC-types or the like, and cabling 16 for coupling sensing device 20 to measuring instrumentation 3. Since measuring instrumentation 3 in this first exemplary embodiment of the system 100 of the present invention is a conventional vibration analyzer, it has an internal power supply capable of powering sensing device 20. When sensing device 20 is activated by vibration analyzer 3, vibration analyzer 3 receives detection signals from the sensing device 20 and operates to display perceptible output, such as waveform 7, on its display 9 which is indicative of the detected sound wave levels internal to the machinery.

Through use of system 100, individuals such as maintenance personnel can assess the functionality of machinery by measuring internal sound wave levels attendant therewith. Depending on the type of machinery being tested, it is recognized that a certain level of internally propagating sound waves may be expected such that the equipment can be diagnosed to ascertain whether acoustic sensing device 20 detects sound wave levels which are outside normal parameters. In other situations, it may be important to ensure there is no internal sound propagating within the machinery, such that any detection signals generated by acoustic sensing device 20 might be indicative perhaps of the onset of or eminency of machinery malfunction. Further, since the present invention in its various forms is directed at approaches to detecting levels of internal sound waves associated with machinery, it should be appreciated that the use of a vibration analyzer or a spectrum analyzer as illustrated in another embodiment of the invention, are only preferred ways for generating perceptible output associated with detection signals. That is to say, the perceptible output might be in the form of a visual display such as illustrated in FIG. 1, an audible display, or a combination of each, without limiting the various types of measuring instrumentations which could be employed.

Figure 2:
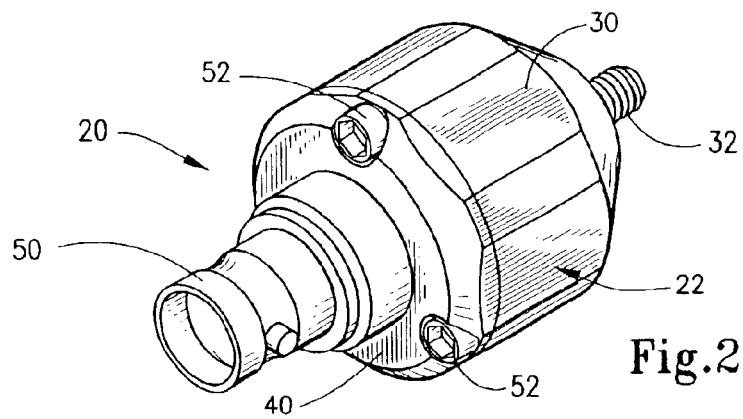
FIG. 2 is an enlarged perspective view of a first exemplary embodiment of an acoustic sensing device of the present invention, which may be used with the system of FIG. 1.
Figure 3:
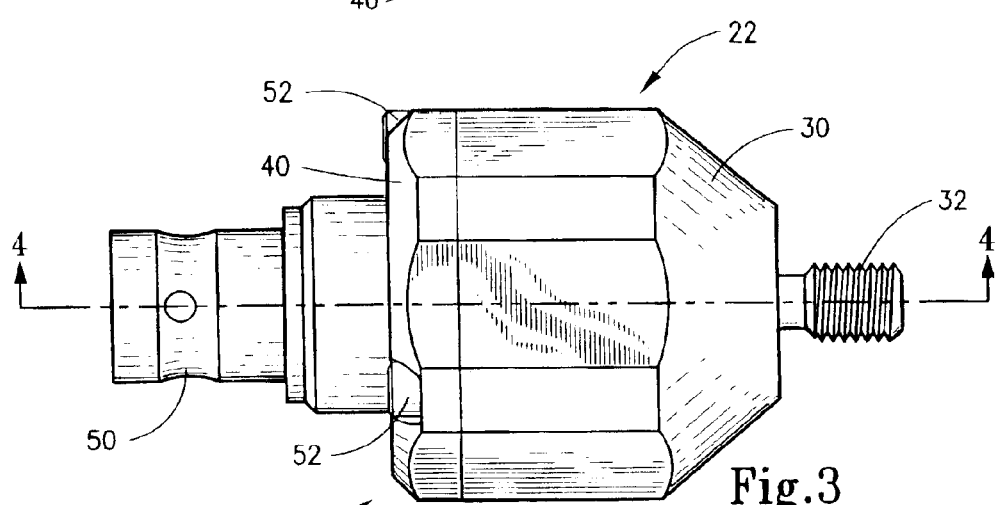
FIG. 3 is an enlarged right side view in elevation of the acoustic sensing device of FIGS. 1 and 2.
Figure 4:
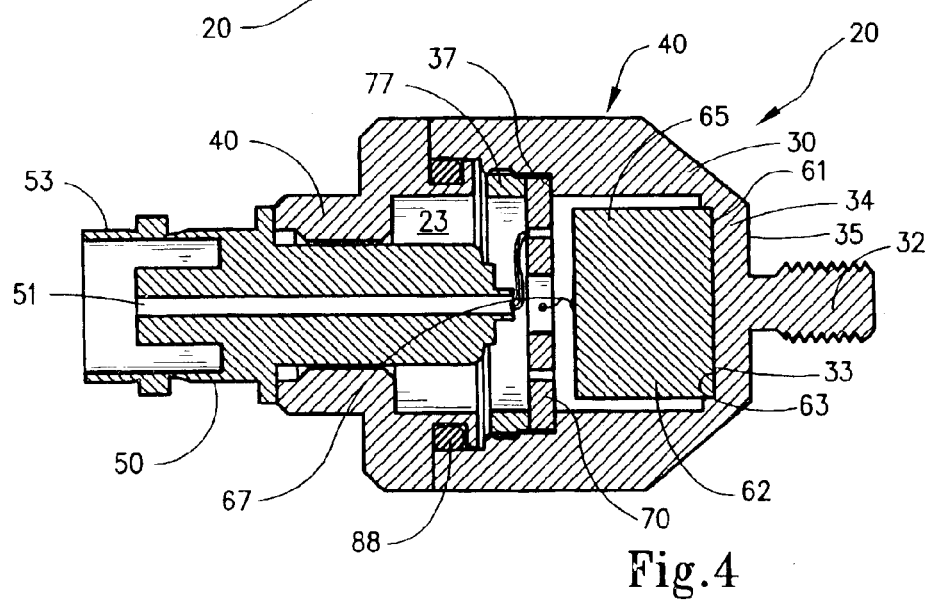
FIG. 4 is a side view in cross-section of the acoustic sensing device as viewed about lines 4—4 in FIG. 3.

A first exemplary embodiment of the acoustic sensing device 20 of the present invention, and that which is depicted in the system 100 of FIG. 1, may now be appreciated with reference to FIGS. 2–5. Acoustic sensing device 20 broadly comprises a housing assembly 22 constructed for removable attachment between the surface mounting region of the machinery and the measuring instrument to define a coupled state, and an acoustic emissions (AE) sensor 60 which is disposed within an interior 23 of housing assembly 22. Housing assembly 22 includes a variety of parts which, together, form an enclosure such that the housing assembly 22 is both electrically and acoustically conductive. In this embodiment of the acoustic sensing device 20 of the present invention, as well as in other embodiments discussed herein, housing assembly 22 includes an arrangement of assembled parts to form the enclosure. It is preferred that housing assembly 22 include a housing body which is adapted for removable attachment relative to the surface mounting region of machinery and a coupler 50, which is shown in FIGS. 2–5 to be in form of a conventional coaxial coupler. The housing body itself includes a main body portion 30 and an end cap 40 attached thereto by appropriate fasteners, such as screws 52. These pieces could also be connected by welding, or the like. When assembled, as shown in FIGS. 2–4, the housing assembly 22 creates an enclosure for the AE sensor 62 and other components of sensing device 20. As shown in various ones of the figures, main body portion 30 is formed to include an integral male threaded projection 32 which is sized and adapted to threadedly engage the correspondingly sized bore 8 shown in FIG. 1 so that sensing device 20 can be directly and removably attached relative to surface mounting region 2. Preferably, projection 22 is a 10/32 threaded stud projection since machinery is commonly known to be manufactured to include correspondingly sized threaded bores.

Main body portion 30 generally tapers in construction toward threaded projection 32 and has a generally circular cross section as shown in the various figures. When mounted in the manner shown in FIG. 1, an end wall 34 of main body portion 30 is in facing relationship with and abuts the exterior surface 6 of surface mounting region 2. End wall 34 preferably has a pair of opposed, substantially planar inner and outer contact surfaces 33 and 35, respectively, as best shown in FIGS. 4 and 7. Outer contact surface 35 preferably abuts the exterior surface 6 of the machinery to maximize the amount of contact between acoustic sensing device 20 and surface mounting region 2 to enhance sound wave transmission and detection. AE sensor 60 is disposed within the interior 23 of the housing body and preferably includes a piezoelectric crystal transducer 62, such as a PZT element available from the Morgan Matroc, Inc. of Scotch Plains, N.J., and appropriate conditioning circuitry (discussed below) contained on a printed wire board 70.

In order to optimize sound level detection, transducer 62 has a mounting face 63 which is adhered to inner contact surface 33 via an appropriate conductive adhesive, such as gold, silver or copper filled epoxy 61. Piezoelectric crystal transducer 62 extends from its mounting face 63 longitudinally within housing interior 23 to terminate in an unrestrained free end portion 65, as best shown in FIG. 4. Circuit board 70 is an annular body which is seated against an internal ledge 37 associated with main body portion 30, and circuit board 70 is sandwiched against ledge 37 by a retainer in the form of a locking ring 77 insertable into housing interior 23 to threadedly engage corresponding threads 38 of main body portion 30 (See FIG. 7). Signals detected from piezoelectric transducer 62 are communicated to the conditioning circuitry by a whisker wire 67 soldered between the unrestrained free end 65 of transducer 62 and an inner conductive ring 75 of circuit board 70. Circuit board 70 also has an outer conductive ring 76 which is in electrical continuity with the wall of main body portion 30 to provide a ground reference for conditioning circuitry 90.

Having described the various components which make up the acoustic sensing device 20, the preferred manner of assembling the device will now be described, primarily with reference to FIGS. 4 and 5. Initially, piezoelectric transducer 62 is glued to the inner contact surface 33 of main housing portion 30 through an appropriate conductive adhesive, as discussed above, after which whisker wire 67 is then soldered in the middle face of the unrestrained free end 65 of transducer 62. Coaxial connector 50 is then inserted into end cap 40 such that it threadedly engages inner threads 42 and thread lock may be used to lock it securely therein. O-ring seal 88 is then placed over the circumferential collar 43 of end cap 40 with the aid of a special lubricant, such as silicone gel, to facilitate placement. O-ring 88 enhances sealing between end cap 40 and main body portion 30. The coaxial connector's tail wire 55, which extends from the coaxial's internal conduit 51, is then passed through retainer 77 and soldered to an appropriate conductive pad 71 formed on circuit board 70. Circuit board is then placed into the interior 23 of main body portion 30 such that the whisker wire from the free face of the crystal passes through the center hole of the circuit board 70 and it is seated against ledge 37. Retainer 77 is then rotated to threadedly engage threads 38 to securely position the circuit board 70 in place in a spaced-apart relationship to piezoelectric crystal 62.

Figures 8, 9:
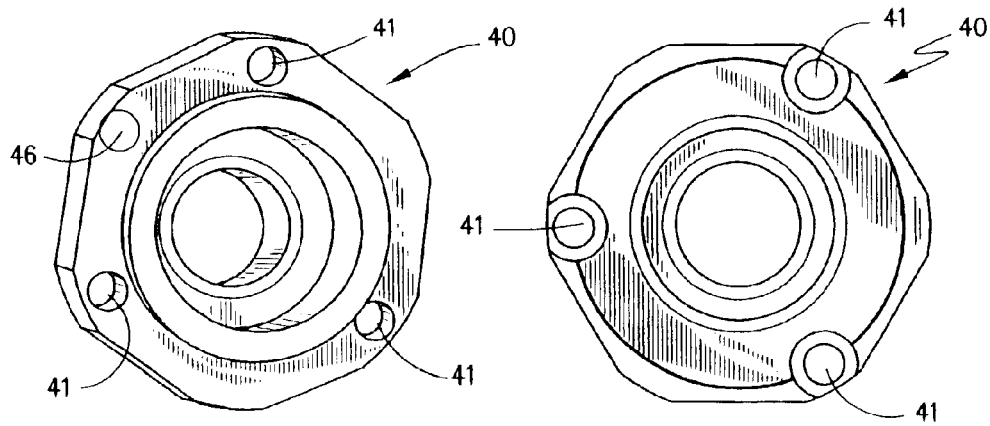
FIG. 8 is an enlarged perspective view of the acoustic sensing device's end cap.
FIG. 9 is a bottom planar view of the end cap.
Figure 10:
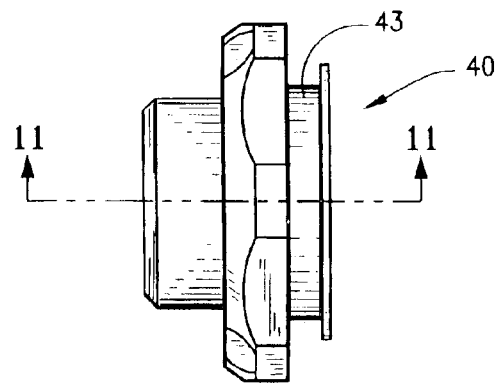
FIG. 10 is a side view in elevation of the end cap.
Figure 11:
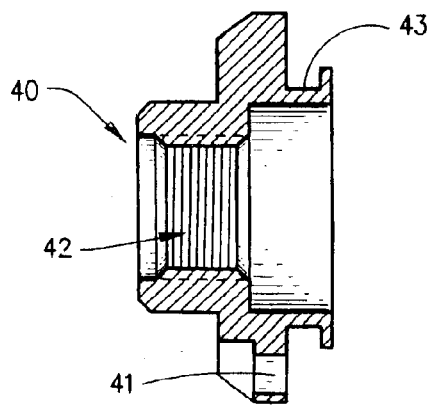
FIG. 11 is a cross-sectional view of the end cap as seen about lines 11—11 in FIG. 10.
Figures 12, 13:
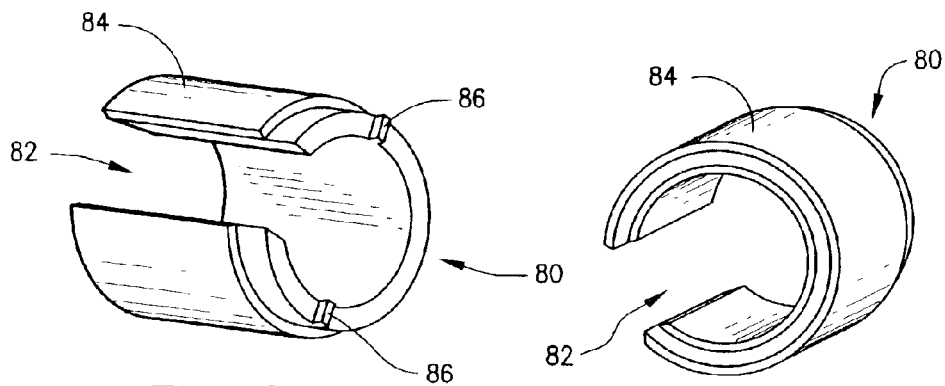
FIG. 12 is an enlarged perspective view of an accessory tool, in the form of a spanner wrench, which may be used during assemblage of the acoustic sensing device of the present invention.
FIG. 13 is another perspective view of the spanner wrench of FIG. 12.

An optional accessory tool, such as spanner wrench 80 shown in FIGS. 12 and 13, can be used to tighten retainer 77 and securely seat circuit board 70 within place against ledge 57. Spanner wrench 80 is a generally cylindrical member having a sidewall 84 which extends around a majority of a circumferential arc to form a slotted channel 82 through which coaxial wire 55 is inserted. Spanner wrench 80 is then positioned so that its protruding nubs 86 register with corresponding notches 78 formed in retainer 77 and thereafter rotated in a clockwise direction to threadedly secure retainer 77 in place. Whisker wire 67 is then soldered to inner annular conductive ring 75. At this point, end cap 40 and main body portion 30 are aligned such that holes 41 formed through end cap 40 are in opposed relationship to threaded holes 31 formed in main body portion 30. As these two sections of the housing assembly are placed together, a conductive spring 79 is oriented between a recess 36 formed in main body portion 30 (FIG. 5) and an opposed recess 46 (FIG. 8) formed in end cap 40. End cap 40 is then attached to main body portion 30 by fasteners 52, as discussed above.

The purpose of compression spring 79 will now be discussed. Since it is important that the housing assembly be electrically conductive, the present invention provides different ways of accomplishing this. For example, both the main body portion 30 and the end cap 40 can be stainless steel bodies such that they are conductive and will provide appropriate shielding. In such a case, there would be no need for compression spring 79. However, in the interest of costs and weight it may be desired to form the housing from aluminum. Further, it is contemplated that the acoustic sensing device will be used in a variety of different environments where it might be exposed to chemicals and other types of unwanted contaminates. Accordingly, it is preferred to anodize the aluminum to provide a protective coating. However, since the housing assembly itself provides both the shielding and the ground reference for the conditioning circuitry, where anodized aluminum is used, spot-faced portions of the end cap 40 and main body portion 30 are not anodized so that spring 79 becomes the electrical connection between these two pieces. The length of the spring's wire is such that, when assembled, spring 79 is fully collapsed to avoid vibration during use and the generation of unwanted noise attendant therewith.

Figure 14:
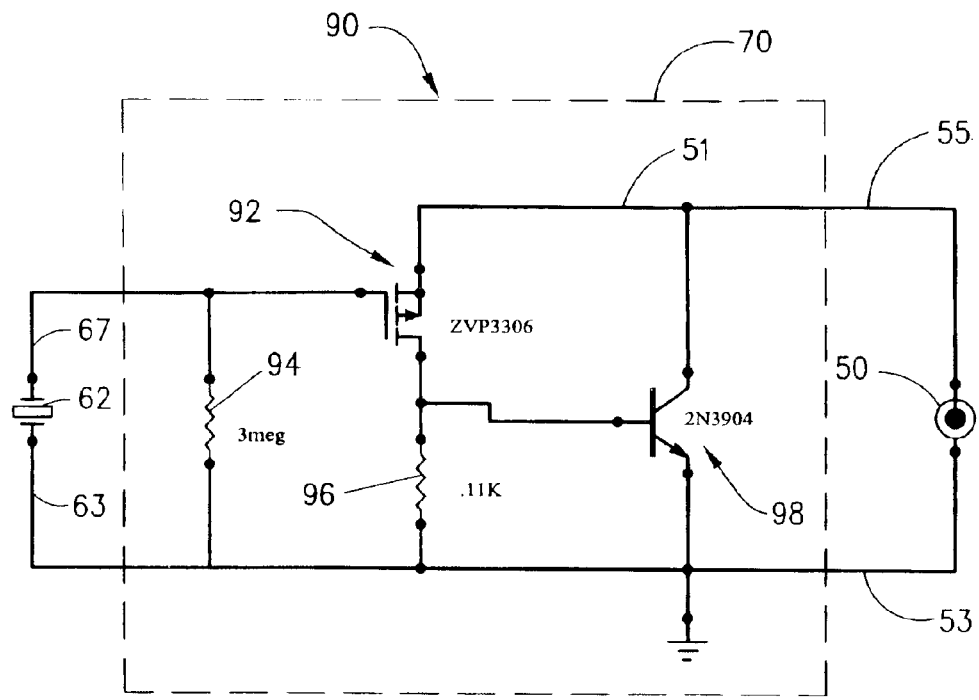
FIG. 14 is a schematic representation of the conditioning circuitry which may be used with the various embodiments of the acoustic sensing device of the present invention.

Having discussed the construction of acoustic sensing device 20 which may be used in system 10 of FIG. 1, the conditioning circuitry 90 thereof will now be described with reference to FIG. 14. With the exception of transducer 62 and coaxial connector 50 all of the various components for the conditioning circuitry 90 (i.e. those within representative boundary box of FIG. 14) are mounted on either one or both sides of circuit board 70 as would be readily appreciated by those skilled in the art of circuit board design. Conditioning circuitry 90 essentially acts as a buffer between transducer 62 and the vibration analyzer. That is, conditioning circuitry 90 has a very high input impedance and a low output impedance while having output detection signals which essentially replicate the input transducer signals from transducer 62. Since the vibration analyzer 20 in FIG. 1 has an associated internal power supply, power to conditioning circuitry 90 is supplied along line 51 in FIG. 14 which corresponds to the connection wire 55 of coaxial connector 50. Ground reference 53 for conditioning circuitry 90 is provided by the coaxial connector's metallic casing which, by virtue of its connection with the unanodized threads 42 of end cap 40, is at the same reference potential as the outer metallic annular ring 76 of circuit board 70 in FIG. 5. The same holds true for the various other components of conditioning circuitry 90 which are grounded to the conductive housing assembly via annular ring 76.

In operation, internal sound waves associated with machinery 14 in FIG. 1 which propagate through region 2 cause crystal 62 to oscillate longitudinally within the housing's interior 23, causing corresponding transducer signals to be generated along whisker wire 67. These input transducer signals are then presented to the gate of MOSFET 92 which is clamped to ground through a high impedance resistor 94 to prevent the gate from drifting. MOSFET 92 is connected like a conventional amplifier circuitry with its source biased at a desired potential, such as 20 volts DC through the vibration analyzer's internal resistance and its drain clamped to ground via resistor 96. NPN transistor 98 is the load for MOSFET 92 with its collector connected to the drain thereof. The emitter of transistor 98 is connected directly to ground. Accordingly, in this more simplified version of the conditioning circuitry 90 which may be used in conjunction with the first exemplary embodiment of the acoustic sensing device of the present invention, MOSFET 92 buffers crystal 62 from the vibration analyzer while providing output detection signals along line 55 which replicate transducer signals on line 67. These detection signals can then be transmitted along the communications interface to the vibration analyzer 20 and be appropriately displayed.

Figures 15, 17:
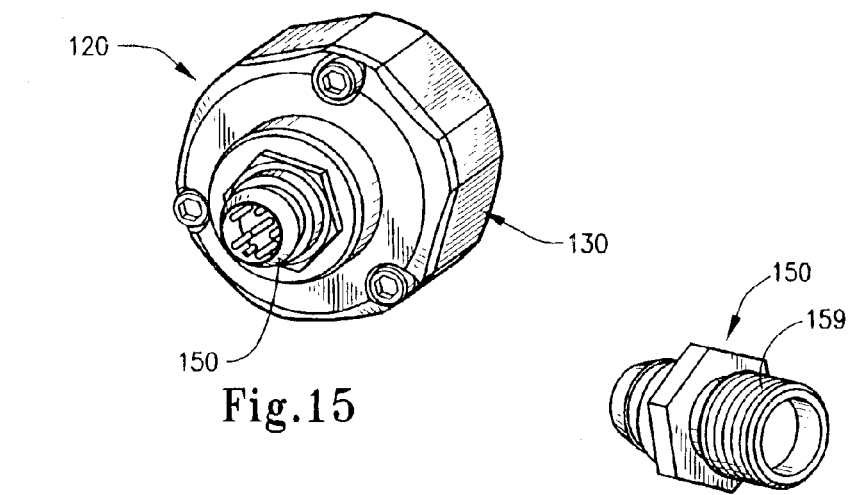
FIG. 15 is a perspective view of a second exemplary embodiment of an acoustic sensing device of the present invention.
FIG. 17 is a perspective view of the multi-pin connector for use with the acoustic sensing device of FIGS. 15 and 16.
Figures 16, 18:
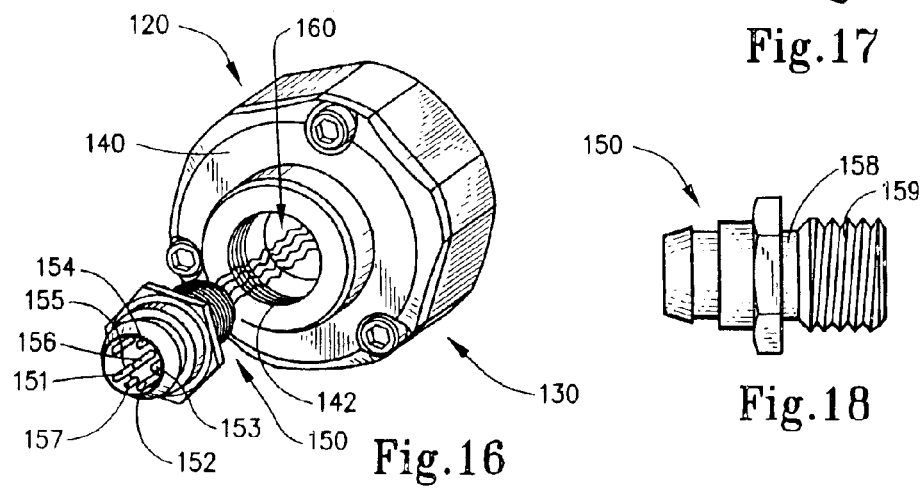
FIG. 16 is an exploded perspective view of the acoustic sensing device of FIG. 15, with the multi-pin connector thereof detached.
FIG. 18 is a side view in elevation of the multi-pin connector.

A second more versatile embodiment for the acoustic sensing device of the present invention is introduced with reference to FIGS. 15 and 16. Here, acoustic sensing device 120 is constructed the same as acoustic sensing device 20 with the exception of its coupler and conditioning circuitry. Accordingly, the discussion of its housing assembly 130 and associated internal components need not be repeated. The coupler for acoustic sensing device 120 in this second exemplary embodiment is in the form of a conventional multi-pin connector 150, such as the MFS Series six-pin connector available from The Turck Corporation. The construction of multi-pin connector 150 may be best appreciated with reference to FIGS. 16–18 which show that it has a threaded extension 159 which is sized to threadedly engage the internal threads 142 of end cap 140 as discussed above with reference to the first exemplary embodiment of the acoustic sensing device. An O-ring (not shown) is preferably inserted over the coupler's collar 158 to hermetically seal it to end cap 140. Multi-pin connector 150 includes a plurality of protruding prongs 151–156 which register, by virtue of key tab 157, with an appropriately configured and conventional cable plug thereby to interface acoustic sensing device 120 with the measuring instrumentation, whether it be a vibration analyzer having an associated power supply, a spectrum analyzer requiring an auxiliary power supply, or other appropriate instrumentation.

Figure 19:
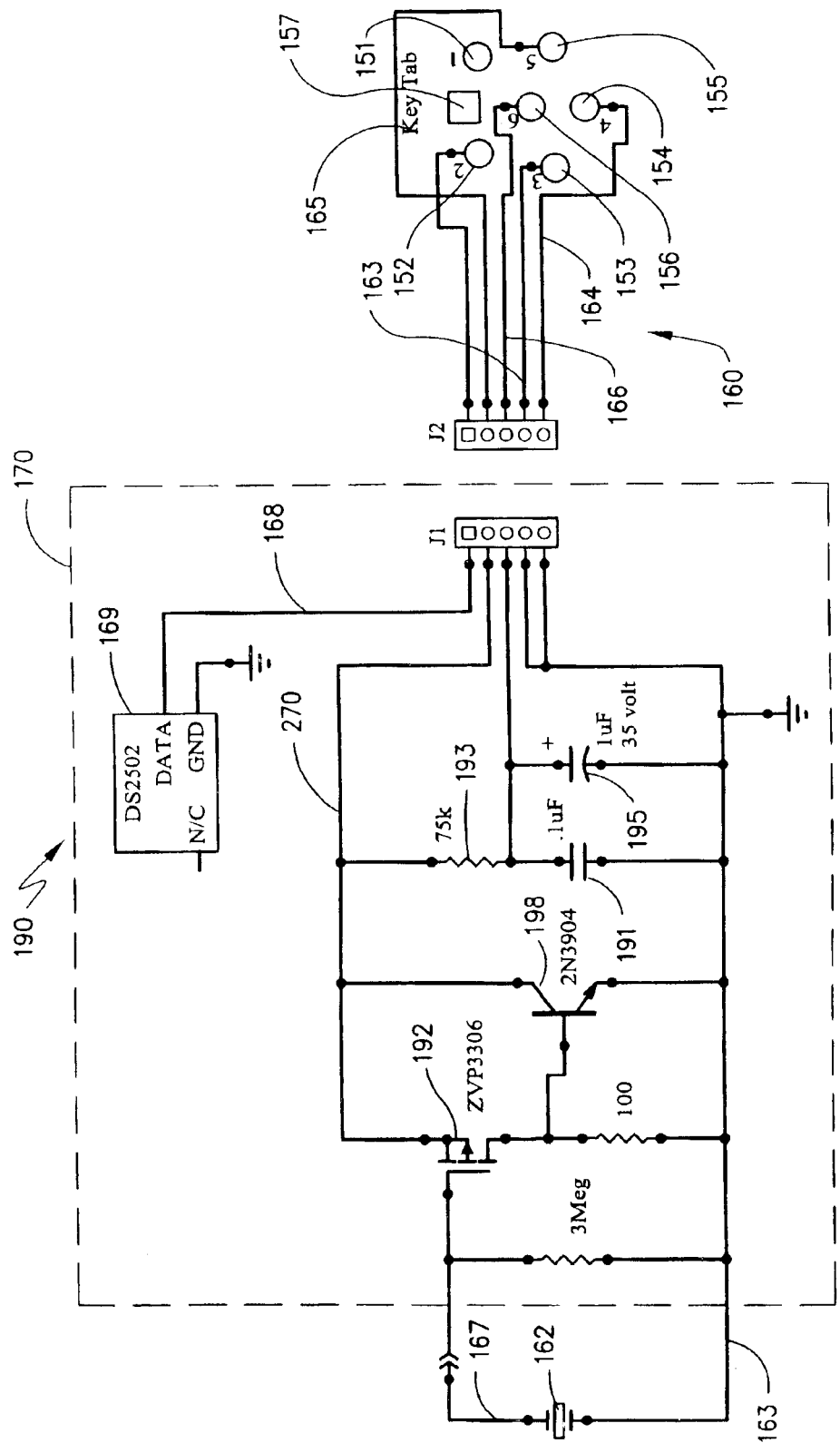
FIG. 19 is a schematic representation of the conditioning circuitry which may be used for the second exemplary embodiment of the acoustic sensing device of the present invention.

A plurality of wires, generally shown by the designation 160 in FIG. 16, are connected to associated ones of prongs 153–157 and extend within the housing assembly's interior to appropriate connection points on the circuit board, as best illustrated with reference to the circuit diagram of FIG. 19 which shows the conditioning circuitry 190 for sensing device 120. In FIG. 19, wires 160 are electrically interconnected to the various circuitry components by virtue of conductive access pads/holes formed in the circuit board 170, the substrate of which may be the same as that of circuit board 70 above. That is, as shown above in FIG. 5, circuit boards 70 and 170 may be formed to include a plurality of small plated bores, schematically represented by "J1" in FIG. 19, to which the ends of wires 160 may be soldered. Once connected in such a manner, wires 163 and 164 are connected directly to ground, while wire 166 which provides power to conditioning circuitry 190 is coupled to ground via filtering capacitors 191 and 195. Wire 166 is also connected to the source of MOSFET 192 and the collector of transistor 198 via load resistor 193. Wire 168 is connected to a serial number ROM 169 which is used to uniquely identify each sensor. The ROM is a serial I/O device such as the DS2502 made by Dallas Semiconductor of Dallas, Tex. Conditioning circuitry 190 operates similarly to conditioning circuitry 90 discussed above such that output detection signals from the conditioning circuitry 190 are communicated to the measuring instrumentation via wire 165 and the appropriate communications interface.

From the above discussion of the conditioning circuitry 190 of the present invention, it should be readily appreciated that the same circuit board can be manufactured for the various acoustic sensing devices of the present invention, whether it be acoustic sensing device 20 or acoustic sensing device 120. To illustrate this, reference is now made to FIG. 20 which shows the same conditioning circuitry 290 adapted for use with the coaxial connector of the first exemplary embodiment of the acoustic sensing device 20 of the present invention. Here, conditioning circuitry 290 is the same as that discussed with reference to FIG. 19 when the coaxial connector is coupled, however, only one wire need be soldered to the appropriate conductive pad of the circuit board when assembled.

Figure 21:
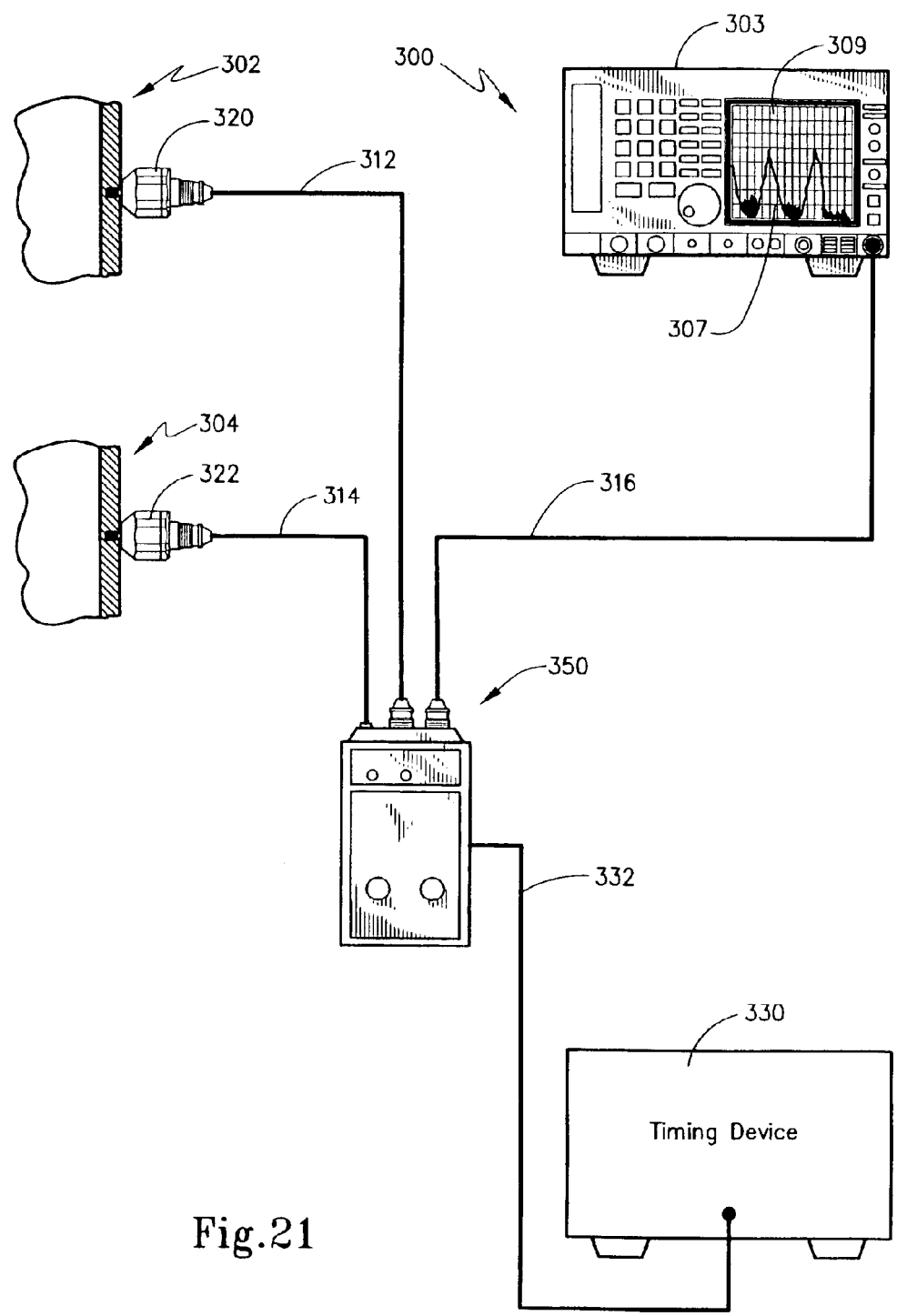
FIG. 21 is a diagrammatic view of a second exemplary embodiment for a system for monitoring acoustic emissions from machinery.

A second exemplary embodiment for a system 300 for detecting sound wave levels associated with equipment is diagrammatically illustrated in FIG. 21. System 300 includes a plurality of sensing devices 320 and 322 which are removably attached relative to respective surface mounting regions 302 and 304 of machinery. Surface mounting regions 302 and 304 may be associated with the same piece of equipment or different pieces of equipment. Additionally, although system 300 incorporates a pair of acoustic emissions sensors 320 and 322, it is contemplated that one of these sensors could be replaced by another type of sensor, such as an accelerometer, so that one sensor detects sound waves propagating internally of equipment, while the other sensor detects internal vibrations associated with the equipment. Each of sensors 320 and 322 is interfaced with measuring instrumentation 303 through a switching device 350. More particularly, acoustic sensing device 320 is coupled to one input of the switching device 350 via communications interface 312, which may be a coaxial coupling as shown, while acoustic sensing device 322 is coupled to another input of switching device 350 via communications interface 314, which may be a multi-pin connector as shown. The output of switching device 350 is then connected to the input of measuring instrumentation 303 via communications interface 316, which may be a coaxial connector as shown.

The measuring instrumentation 303 for use in system 300 may be, as discussed above with reference to system 100, a vibration analyzer which has its own internal power supply to be used to power sensors 320 and 322. Alternatively, measuring instrumentation 303 may be of a type which does not have its own internal power supply, such as a spectrum analyzer, with power to sensors 320 and 322 supplied by switching device 350. For purposes of the description of system 300 and its associated switching circuitry, it will be assumed that measuring instrumentation 303 is in the form of a spectrum analyzer. In any event, switching device 350 is selectively operative to couple the outputs of either sensor 320 or 322 to the input of measuring instrumentation 303 such that the detection signals generated by the selected sensor 320 or 322 is displayed as a waveform 307 on the measuring instrumentation's display 309. Again, depending on the type of measuring instrumentation employed, it can take on a variety of configurations such as that depicted in FIG. 21. Alternatively, it can be a smaller handheld device or even a portable laptop computer, or the like. Also depending on the type of measuring instrumentation employed, it may have a variety of display capabilities so that it plots the amplitude of the detected signals as a function of frequency or, perhaps, the amplitude of the detected signals as a function of time.

System 300 also provides for the capability of monitoring detected signals from the selected sensor 320 or 322 at desired times by interfacing the switching device 350 to a timing device 330, as diagrammatically illustrated in FIG. 21. Timing device 330 may, for example, be a stroboscope or other appropriate device which interfaces with switching device 350 via communication line 332 and operates to only allow detected signals to pass through to the measuring instrumentation 303 at desired time intervals. For instance, it may be desirable to monitor the activity of a diesel engine's cylinders through the use of sensing devices 320 or 322. However, without using a timing device to latch the detected signals at appropriate times, the contribution from each of the cylinders would be superimposed with the composite output displayed on measuring instrumentation 303. However, using a timing device, a particular cylinder of interest can be isolated from the others so that when this cylinder, for example, is at top dead center stroboscope 330 can generate a timing signal synchronized to this position so that the output from the switching device is correspondingly synchronized.

Figure 22:
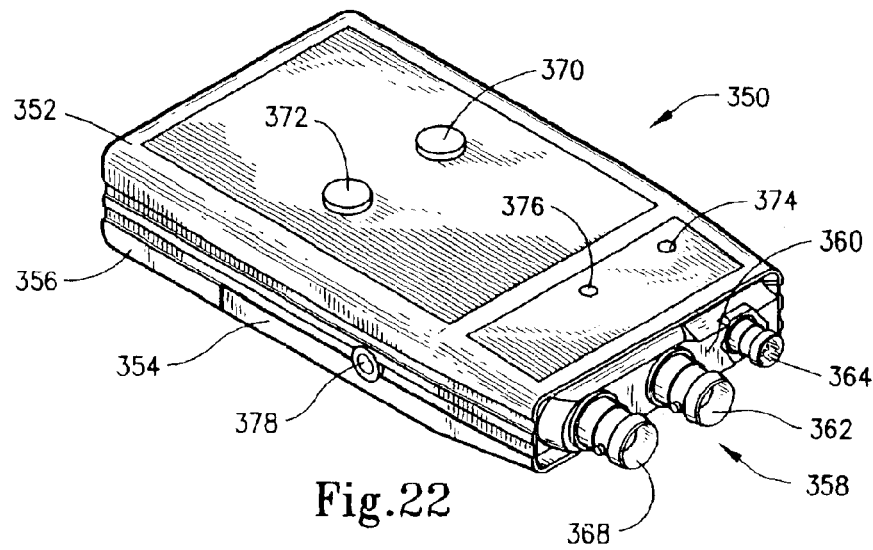
FIG. 22 is a perspective view of a casing which houses the switching circuitry associated with the system of FIG. 21.
Figure 44:
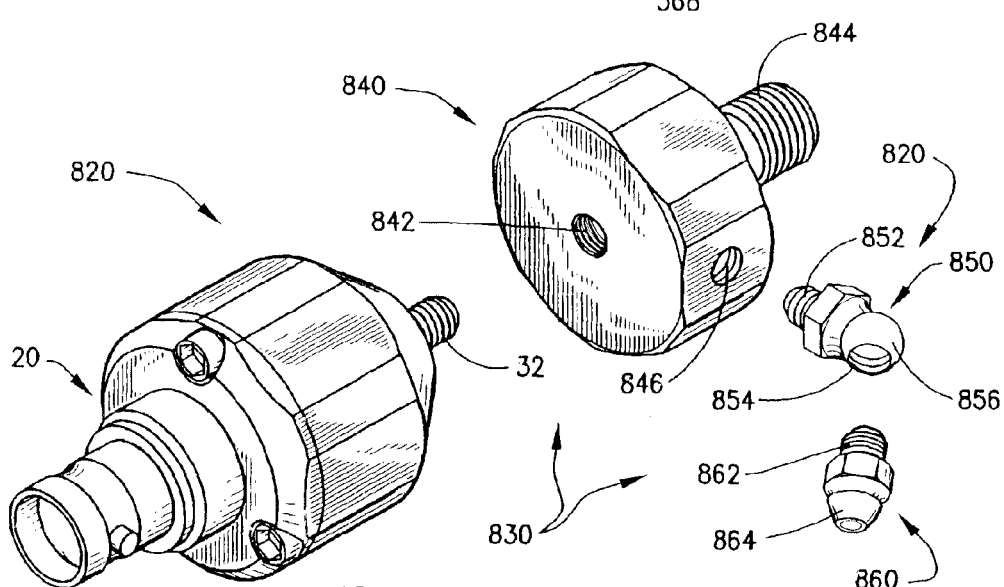
FIG. 44 is an exploded perspective view of the acoustic sensing device shown in FIG. 43.

Switching device 350 has associated switching circuitry which may be housed in a casing as shown in FIG. 22. The particular construction of such a casing and the housed circuit board(s) which support the associated switching circuitry supported within the casing would be well within the purview of the ordinarily skilled person. Accordingly, while FIG. 22 shows a representative construction for the casing for switching device 350, it should be readily appreciated that any of a variety of different types of constructions would be contemplated without departing from the inventive concepts herein. This casing may include top and bottom covers 352 and 350 which lockingly engage one another and a battery cover 356 providing access to a battery compartment which houses a 9 volt battery for supplying power to the switching circuitry. The front end portion 358 of switching device 350 includes a panel 360 to which is mounted a pair of coaxial connectors 362 and 364 and a multi-pin connector 364, to which the two sensors and the measuring instrumentation can be coupled through appropriate known and readily available interface connections. Activation of the switching device 350 is provided by an on/off push button switch 370, and a sensor select switch 372 is provided which operates upon activation to selectively interconnect the measuring instrumentation to the output of a selected one of the sensing devices. Switching device 350 also includes a pair of indicator lights 374 and 376 so that an operator is given visual confirmation of which sensing device is coupled to the measuring instrumentation at any given time. A conventional stereo jack input 378 is provided to interconnect the unit to a timing instrument, such as the stroboscope 330 shown in FIG. 21.

Figure 23:
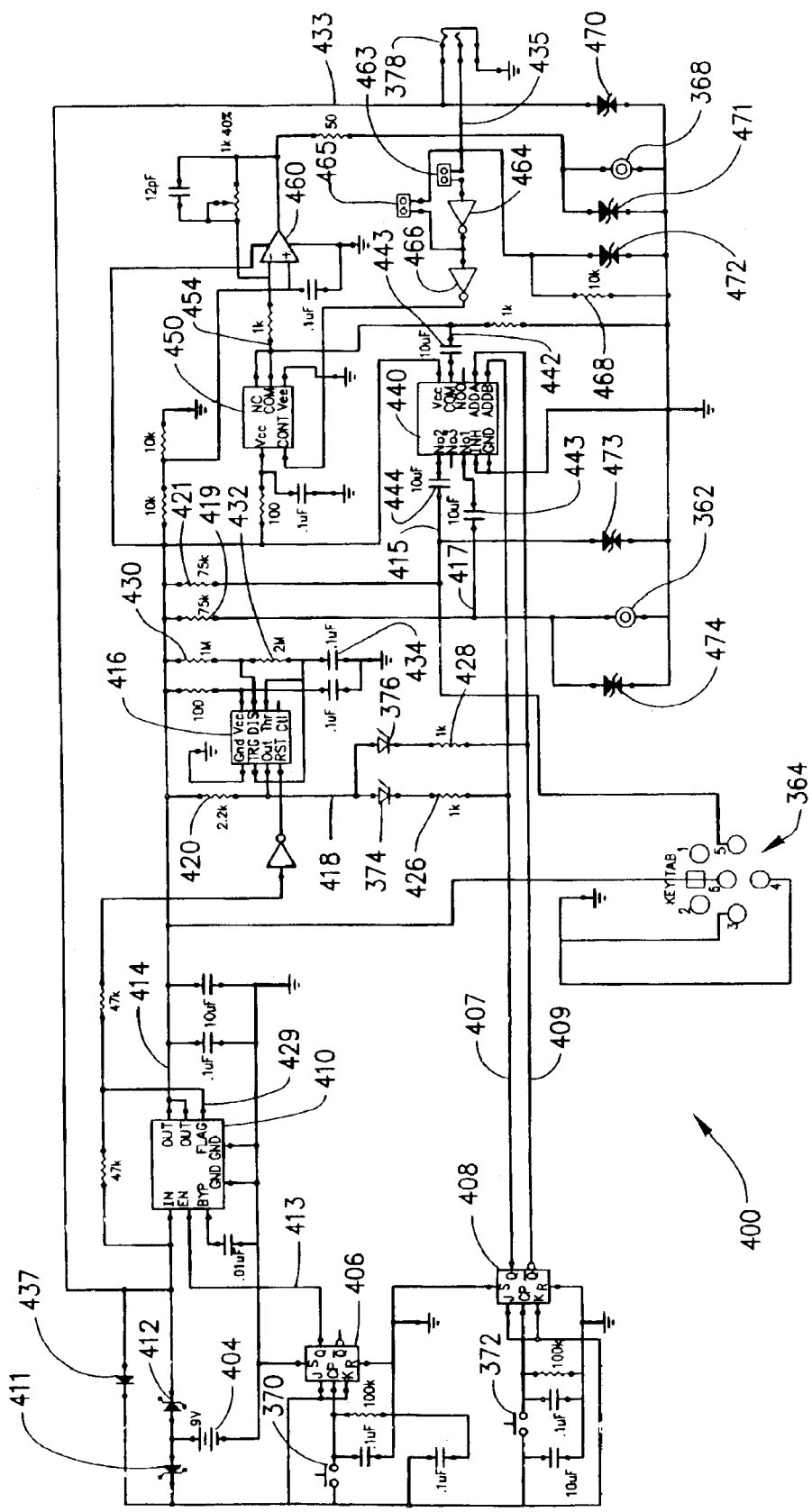
FIG. 23 is a schematic representation of the switching circuitry for use with the system of FIG. 21.
Figure 24:
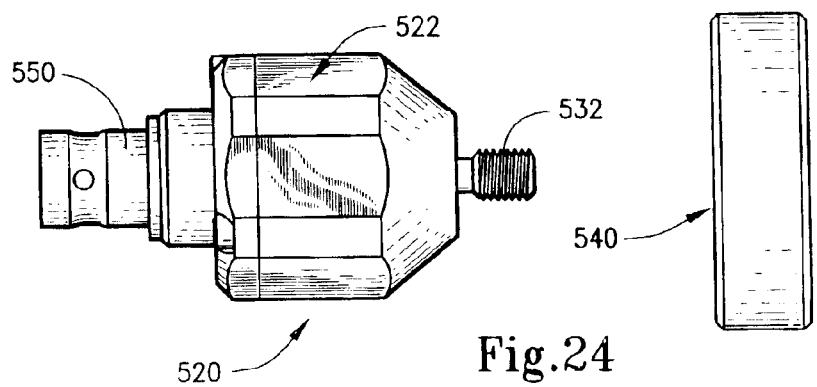
FIG. 24 is an exploded side view in elevation illustrating a first exemplary embodiment of mounting adapter which may be used with the various acoustic sensing devices of the present invention, and particularly illustrating its use with the acoustic sensing device according to the first exemplary.
Figure 25:
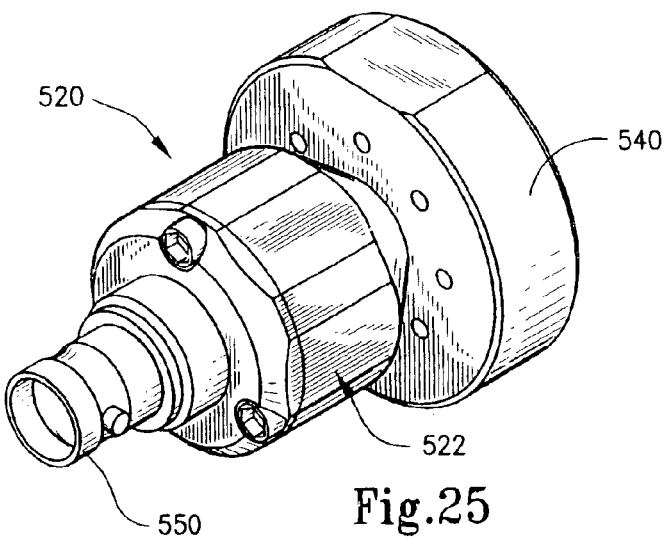
FIG. 25 is a perspective view of the mounting adapter mounted on the acoustic sensing device.

FIG. 23 is a schematic of the preferred switching circuitry 400 that is contained within the housing of switching device 350. Switching circuitry 400 may be powered internally and operates upon actuation to pass conditioned detected signals from a selected one of its coaxial input 362 or multi-pin input 364 through switching and amplification circuitry to produce conditioned output signals along its coaxial output 368 for communication to the measuring instrumentation. Switching circuitry 400 can also be powered externally through the same stereo jack 378, if desired.

Internal power for switching circuitry 400 is provided by a 9 volt battery 404 which is connected to a pair of J-K flip flops 406, 408 and a voltage regulator 410. Schottky diodes 411–412 are provided to isolate battery 404 from any external power source that is used. When wired as shown, actuation of on/off push button switch 370 toggles the state of flip flop 406 and causes a logic "high" to be produced at its output 413 which is connected to the enable input of voltage regulator 410. Regulator 410, which is preferably a MIC52065.OBMM available from Micrel, Inc. of San Jose, Calif., accordingly produces a regulated DC output of approximately 5 volts along its output line 414. This provides power to the rest of the circuitry components in FIG. 23, as well as the sensor(s) connected at inputs 362 or 364. As can be seen, since the "J" and "K" inputs of flip-flop 406 are tied together, subsequent activation of push button 370 will disable the flip-flop as well as the regulator, thus deactivating switching circuitry 400.

Flip flops 406 and 408 are preferably contained on a common integrated circuit chip such as the CD4027BCN available from Fairchild Semiconductor of South Portland, Me., or others readily available. Second flip-flop 408 is provided to selectively toggle which of the detected signals from sensor 362 or 364 will be passed through coaxial output 368. Flip-flop 408 has an associated push button selection switch 372 and, likewise, has its "J" and "K" inputs tied together so that each time switch 372 is pushed it alters the state of it's outputs.

A low battery indication is provided by a timer 416 which is powered by the regulator's output on line 414. Timer 416 is preferably an LM555CN, also available from Fairchild Semiconductor. Under normal battery conditions, timer 416 outputs a logic high along output line 418 which is tied to the 5 volt power supply from regulator 410 via resistor 420. Output line 418 of timer 416 is also connected to the anodes of LED's 374 and 376 which, respectively, have their cathodes connected to output lines 407 and 409 of flip-flop 408 via resistors 426 and 428. Accordingly, when the battery is functioning properly, output line 418 of timer 416 and, thus, the anodes of diodes 374 and 376 are at a logic level "high". Depending on which of the inputs 362 and 364 is selected by J-K flip-flop 408, one of its outputs 407 and 409 goes "low" resulting in an illumination of a corresponding one of diodes 374 and 376. For example, selection of coaxial input 362 is accomplished by pushing switch 372 until output line 409 of flip-flop 408 goes low resulting in illumination of diode 376 thereby to indicate this selection. However, were battery 404 to be drained, this would cause a resulting flag signal to be generated along output line 429 of regulator 410 which, by virtue of inverter 430, causes a logic level "high" to be seen at the reset input of timer 416. In this situation, timer 416 would then generate a pulsating output along line 418 having a frequency determined by resistors 430, 432 and capacitor 434. This pulsating output causes the associated one of LEDs 374 and 376 to flash accordingly, thereby indicating to the user that battery 404 may need replacement.

The outputs of J-K flip-flop 408 are also connected to the inputs of a first normally open switch 440, such as the MAX4524 available from Maxim Integrated Products of Sunnyvale, Calif. Switch 440 is operative, depending upon which of its inputs 407 and 409 is at a logic level "low" to couple detected input signals along lines 415 and 417 to its output 442. For example, and assuming again that the coaxial input 362 has been selected by J-K flip-flop 408, a logic level "low" is seen on line 409 which causes first switch 440 to communicate input detection signals from line 417 to its output along line 442. It should be noted that resistors 419 and 421 are present to provided the necessary biasing for the MOSFET associated with the particular sensor's conditioning circuitry (see FIGS. 14, 19 & 20, above). Large coupling capacitors 443 and 444 are also provided to ensure that these signals are passed through first switch 440 without attenuation.

Output 442 of first switch 440 is connected to the input of a second switch 450 and to ground via bleeding capacitor 443. Second switch 450 is preferably a MAX4517, also available from Maxim Integrated Products. The "control" input 452 of second switch 450 is normally low unless a stroboscope or other appropriate timing device is connected via jack 378. Accordingly, assuming no such timing device is connected, output signal 442 continuously passes through normally closed switch 450 along output line 454 and is presented to amplifier 460. Amplifier 460, such as an LM7121 available from National Semiconductor, operates to compensate for all attenuations and losses through switches 440 and 450 since these switches have different "on" resistances. Amplifier 460 is wired for negative feedback and essentially acts like a gain trimmer which communicates output signals along line 462 to coaxial output 416.

As stated above with reference to FIGS. 21 and 22, the switching device 350 of the present invention and its corresponding switching circuitry 400 can be interfaced with a stroboscope or other appropriate timing device via stereo jack 378. If such is the case, one of the jack's input lines 433 can be used as an external power line to activate regulator 410 and flip-flops 406 and 408, as shown. This power line 433 may be interfaced to the inputs of flip-flops 406 and 408 via a diode 437. The timing signal from the stroboscope can be presented to switching circuitry 400 along input line 435 which is coupled to second switch 450 via Schmidt Triggers 464 and 466 which operate to square the edges of the incoming timing signals so that it is not susceptible to noise. This timing signal then provides the control for second switch 450 and, correspondingly causes the output of second switch 450 to transition accordingly. As stated above with reference to FIG. 21, this can be useful if it is desired to synchronize the output of switching circuitry 400 with the particular activity of a moving part of a machinery which is being tested. Jumpers 463 and 465 may be provided on the circuit board associated with switching circuitry 400 to provide the capability of ensuring that the control input of second switch 450 goes "high" regardless of the polarity of the incoming pulse from the stroboscope on line 435. As can be seen, input line 435 from the stroboscope is also connected directly to ground via resistor 468 to ensure that a driving force along line 435 must be present in order to cause the control input 452 of second switch 450 to go "high". As shown, a plurality of transient suppressors 470–474, such as the LCDA series of TVS arrays available from the Semtech Corporation of Newbury Park, Calif., may also be included to protect switching circuitry 402 against zapping.

Figure 20:
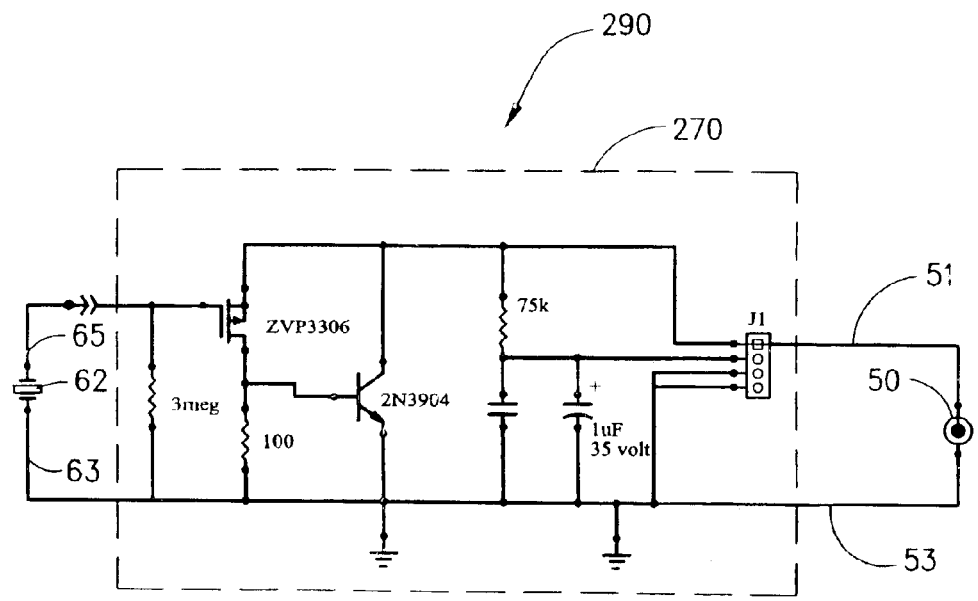
FIG. 20 is a schematic representation of the same conditioning circuitry of FIG. 19, but showing its use with the coaxial connector associated with the first exemplary embodiment of the acoustic sensing device of the present invention.

With the above description in mind for the switching circuitry 400, as well as the conditioning circuits discussed with reference to FIGS. 14, 19 & 20, the ordinarily skilled artisan in circuit design should readily appreciate that a variety of circuitry variations could be implemented without departing from the concepts contained herein. For example only, the switches 440 and 450, can be electromechanical relays and an appropriate microcontroller could be utilized in place of the various circuitry elements shown in FIG. 23.

Reference is now made to FIGS. 24–36 to discuss various types of mounting adapters which may be used to releasably attach the acoustic sensing device's housing assembly to the surface mounting region of machinery. It is recognized that there may be certain situations in which the acoustic sensing device of the present invention, such as any of the embodiments thereof as discussed above, is not capable of directly attaching to the surface mounting region of machinery. This might arise, for example, if the machinery is provided with a threaded access bore which is not sized to accommodate the threaded mounting projection formed on the housing assembly's main body portion. This might also arise if the surface mounting region of interest on the machinery is itself provided with a threaded stud as opposed to a threaded bore. It also may be that the surface mounting region of interest is not provided with any kind of attachment structure. Accordingly, the present invention contemplates a variety of different types of mounting adapters which permit the acoustic sensing device to be removably attached to the surface mounting region of equipment in any one of the above-noted circumstances.

A first type of mounting adapter is shown in FIGS. 24–27. In these figures, the mounting adapter 540 is in the form of a puck-shaped member having a threaded bore 542, preferably of a 10-32 thread size, for receiving the threaded mounting projection 532 associated with the housing assembly 522 of sensing device 520. The bottom of mounting adapter 540 is formed to include a plurality of cylindrical cavities 544 which are spaced equiangularly around its center, with each cavity adapted to a receive magnetic element Preferably, each of the magnetic elements is formed of rare earth materials such as neodymium. A plurality of punch-out bores 545 are also provided and extend through adaptor 540 to permit easy removal of the magnetic elements. Accordingly, it may be appreciated that, when sensing device 520 is threadedly attached to mounting adapter 540, the assemblage can then be magnetically and releasably attached to a surface mounting region of machinery where possible. It is preferred that threaded mounting projection 532 extend completely within threaded bore 542 so that it is in close proximity to the surface mounting region when in the mounted state with the outer contact surface 535 in contact with the upper surface 541 of mounting adapter 540, thereby to optimize detection by the sensing device.

Figures 26, 27, 27A:
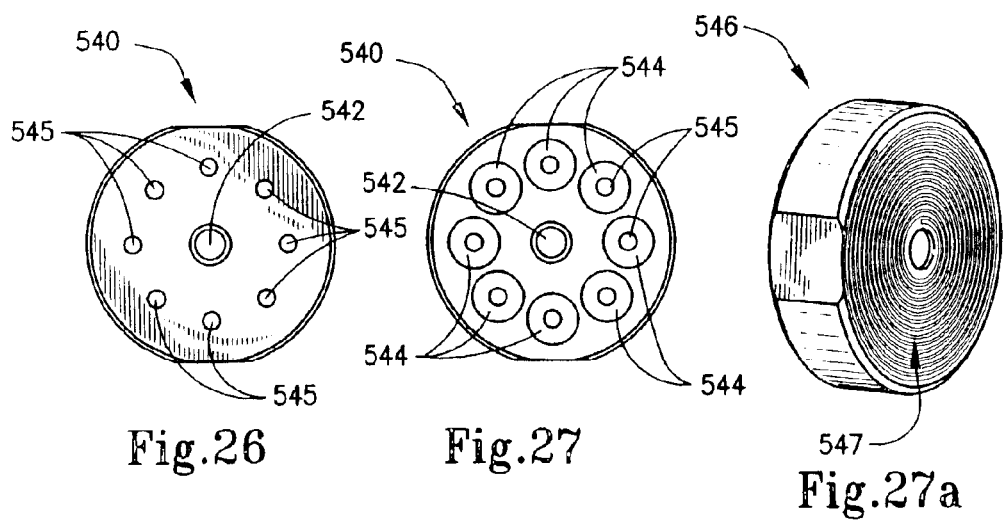
FIG. 26 is a top plan view of the mounting adapter shown in FIGS. 24 and 25.
FIG. 27 is a bottom plan view of the mounting adapter shown in FIGS. 24 and 25.
FIG. 27(a) is a perspective view of an alternative construction for the first exemplary embodiment of a mounting adaptor.

An alternative construction to the mounting adapter is shown if FIG. 27(a). Here, mounting adapter 546 does not incorporate cylindrical cavities or punch-out bores. Instead, mounting adapter 546 is provided with a spiraling groove 547 in it's bottom surface so that adapter 546 can be adhered to a mounting surface with an appropriate adhesive. Of course, concentric grooves or any geometry providing a rough surface texture could replace the spiral groove of FIG. 27(a) to accomplish the same result.

FIGS. 28–36 illustrate mounting adapters which serve as size conversion structures for releasably attaching an acoustic sensing device to a surface mounting region. The mounting adapter constructions shown in FIGS. 28–32 are useful for attaching the sensing device to a surface mounting region which is provided with a threaded access stud projecting therefrom. A first mounting adapter 640 is shown in FIGS. 28–30. As shown in these figures, mounting adapter 640 has a lower nut portion 642 machined to have a size 10-32 threaded bore 643, an upper nut portion 646 machined to have a size ¼-28 threaded bore 645, with a neck region 644 extending therebetween. Accordingly, mounting adapter 640 is useable for removably attaching a sensing device having a size 10-32 male projection, such as those discussed above, onto a surface mounting region having a threaded stud of size ¼-28.

Mounting adapter 650 shown in FIGS. 31 and 32 is similarly constructed in that it also has a lower nut portion 652 machined with a size 10-32 threaded bore 653 for releasably attaching an appropriately sized 10-32 male threaded projection on a sensing device. An opposite second end portion 656 has a size ¼-20 female threaded bore 655 formed therein for threadedly engaging a correspondingly sized male threaded projection extending from the surface mounting region of the machinery. Extending between lower end portion 652 and upper end portion 656 is an enlarged mid-portion 654.

FIGS. 33–36 illustrate mounting adapters for removably attaching a sensing device having a common 10-32 male threaded projection onto surface mounting regions having threaded bores of different sizes. More particularly, in FIGS. 33 and 34 a first such mounting adapter 660 includes a lower end portion 662 having a 10-32 female threaded bore 663 for receiving the sensing device's mounting projection, an upper end portion 665 having size ¼-20 male threads for threadedly engaging a correspondingly sized threaded bore in the surface mounting region, and a neck 664 of reduced thickness extending therebetween. Finally, mounting adapter 670 in FIGS. 35 and 36 has a lower end portion 672 also formed with a 10-32 female threaded bore, an upper end portion 676 having size ¼-28 male threads for threaded engagement in a correspondingly sized female bore associated with the surface mounting region, and a neck 674 of reduced thickness extending therebetween.

Figure 37:
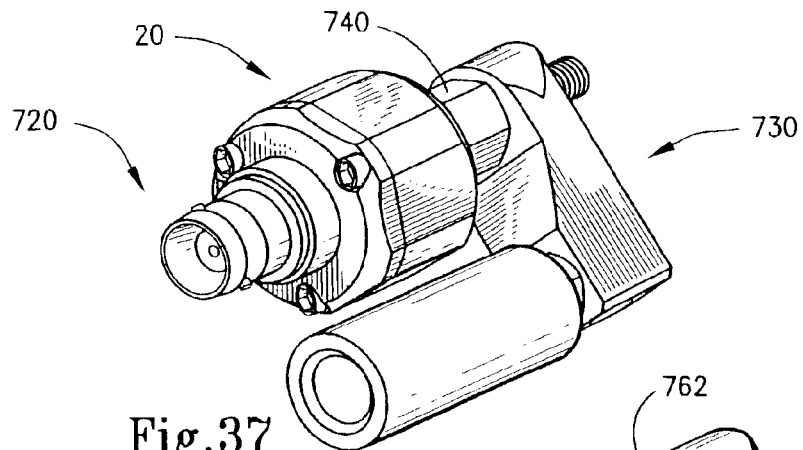
FIG. 37 is a perspective view of a first exemplary embodiment of an acoustic sensing device that is particularly suited for lubricating bearings and for testing bearing failure.
Figure 38:
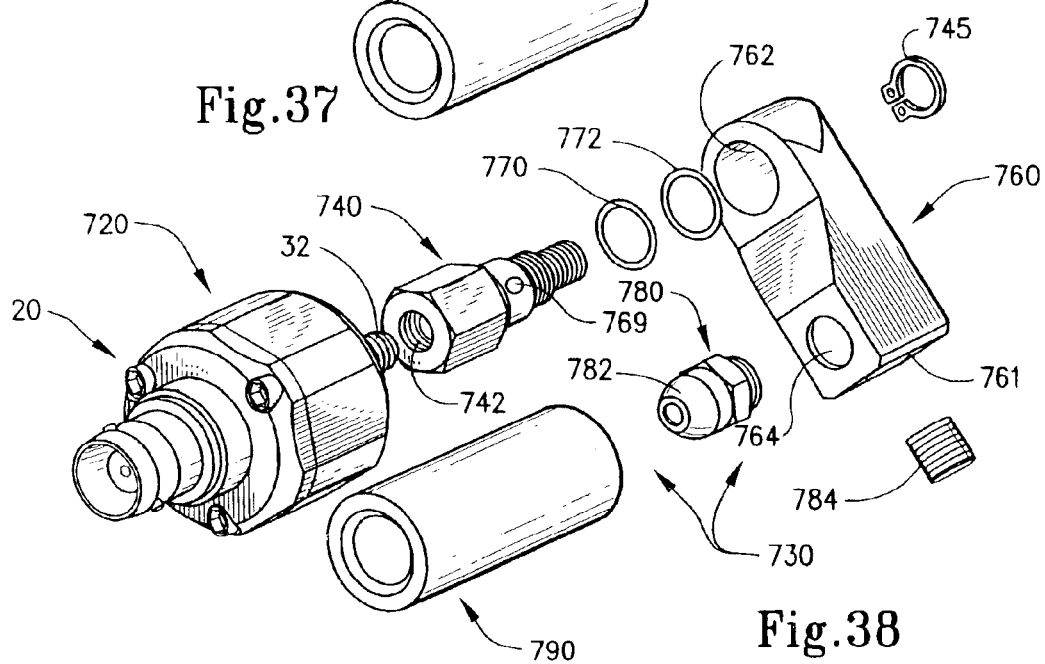
FIG. 38 is an exploded perspective view of the acoustic sensing device shown in FIG. 37.

Other embodiments for AE sensing devices which are particularly suited for testing bearing failure may now be appreciated with reference to FIGS. 37–44. In FIGS. 37 and 38, a first exemplary embodiment for such an acoustic sensing device 720 is shown to include the acoustic sensing device 20, such as described above, and a mounting assembly 730 pivotally disposed thereon for use in injecting grease into a bearing through an appropriate access port formed in a piece of machinery. It should be appreciated that either sensing device 20 or sensing device 120 could be used as a component of sensing device 720. Mounting assembly 730 for sensing device 720 includes a swivel post 740 having a threaded bore 742 sized and adapted to threadedly engage male threaded projection 32 of sensor 20. Threaded bore 742 is formed in a nut-shaped head 744 of swivel post 740 and a swivel body 760 is received on a lower post portion 746 of swivel post 740. More particularly, swivel body 760 has en enlarged hole 762 formed therethrough which is received over lower post portion 746 and retained thereon by a pair of O-rings 770 and 772 which, respectively, seat on circumferential neck regions 741 and 743 of swivel post 740 to provide a sealed engagement between swivel post 740 and swivel body 760. A C-clamp 745 is positioned over a collar 748 on lower post portion 746 to retain swivel body 760 on swivel post 740.

Figures 39, 40:
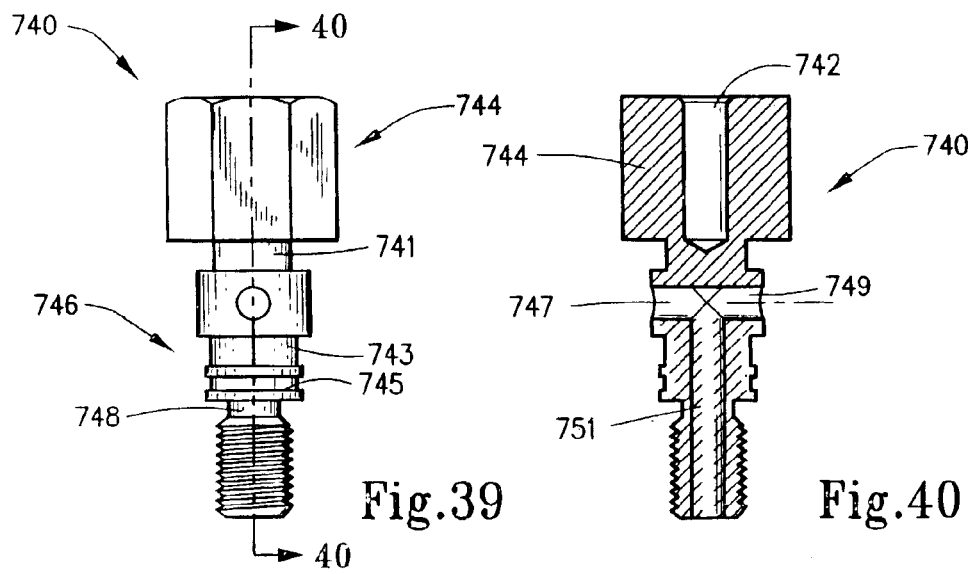
FIG. 39 is a side view in elevation of the swivel post for use with the acoustic sensing device of FIGS. 37 and 38.
FIG. 40 is a cross-sectional view of the swivel body as seen about lines 40—40 in FIG. 39.
Figure 41:
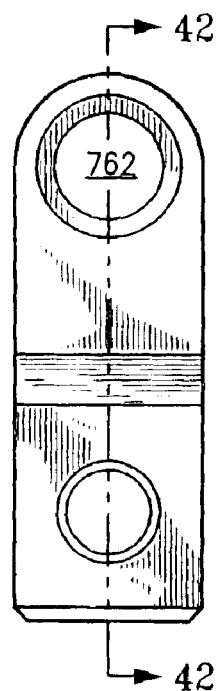
FIG. 41 is a plan view of the swivel body for use with the acoustic sensing device of FIGS. 37 and 38.
Figure 42:
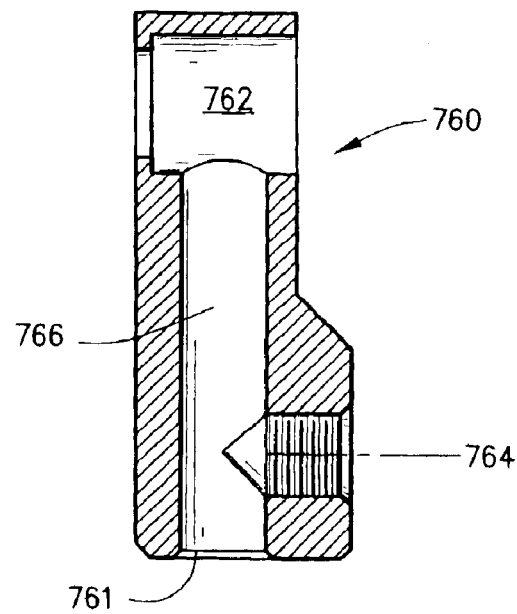
FIG. 42 is a cross-sectional view of the swivel body as seen about lines 42—42 in FIG. 41.
Figure 43:
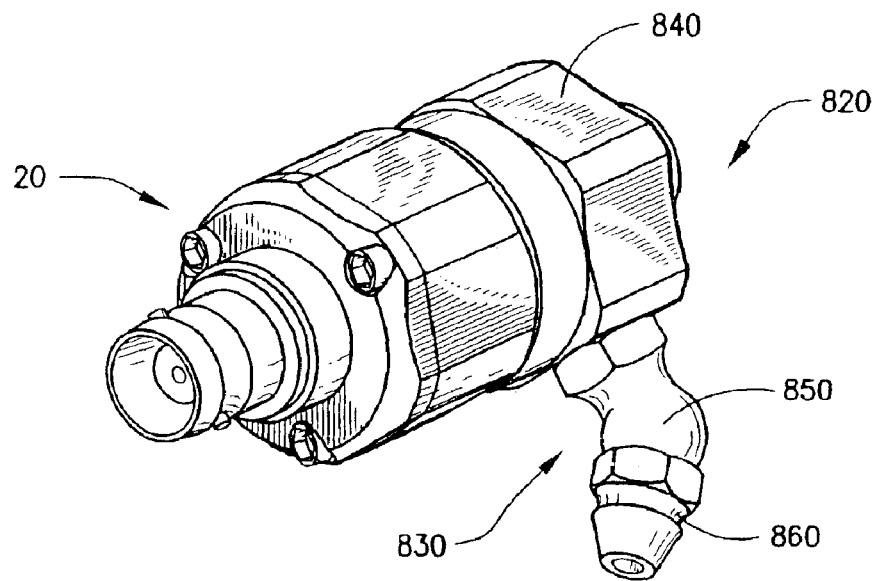
FIG. 43 is a perspective view of a second exemplary embodiment for an acoustic sensing device adapted for use in lubrication of bearings.
Figure 47:
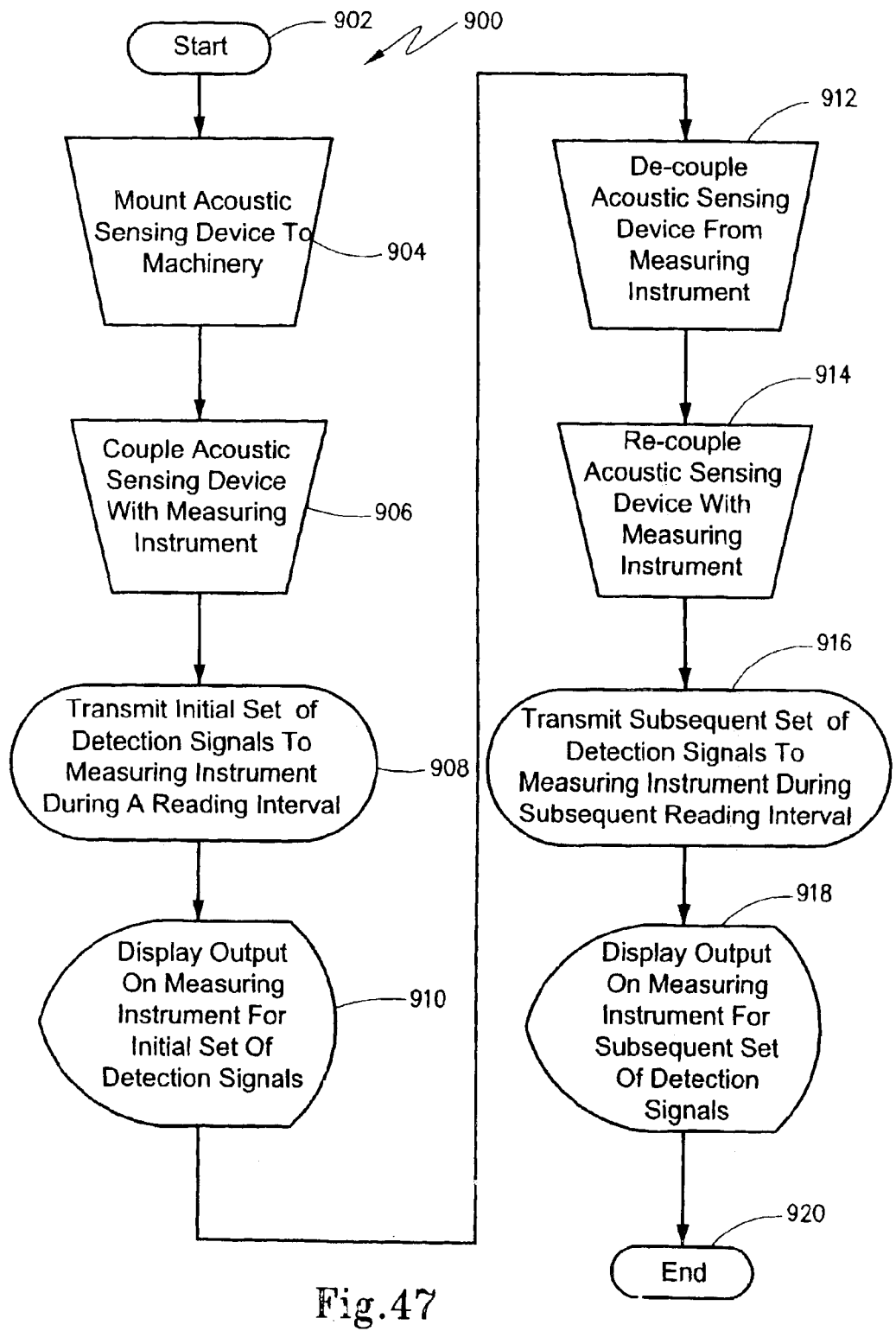
FIG. 47 is a flowchart illustrating the principal concepts for practicing a first exemplary embodiment of the methodology of the present invention.
Figure 48:
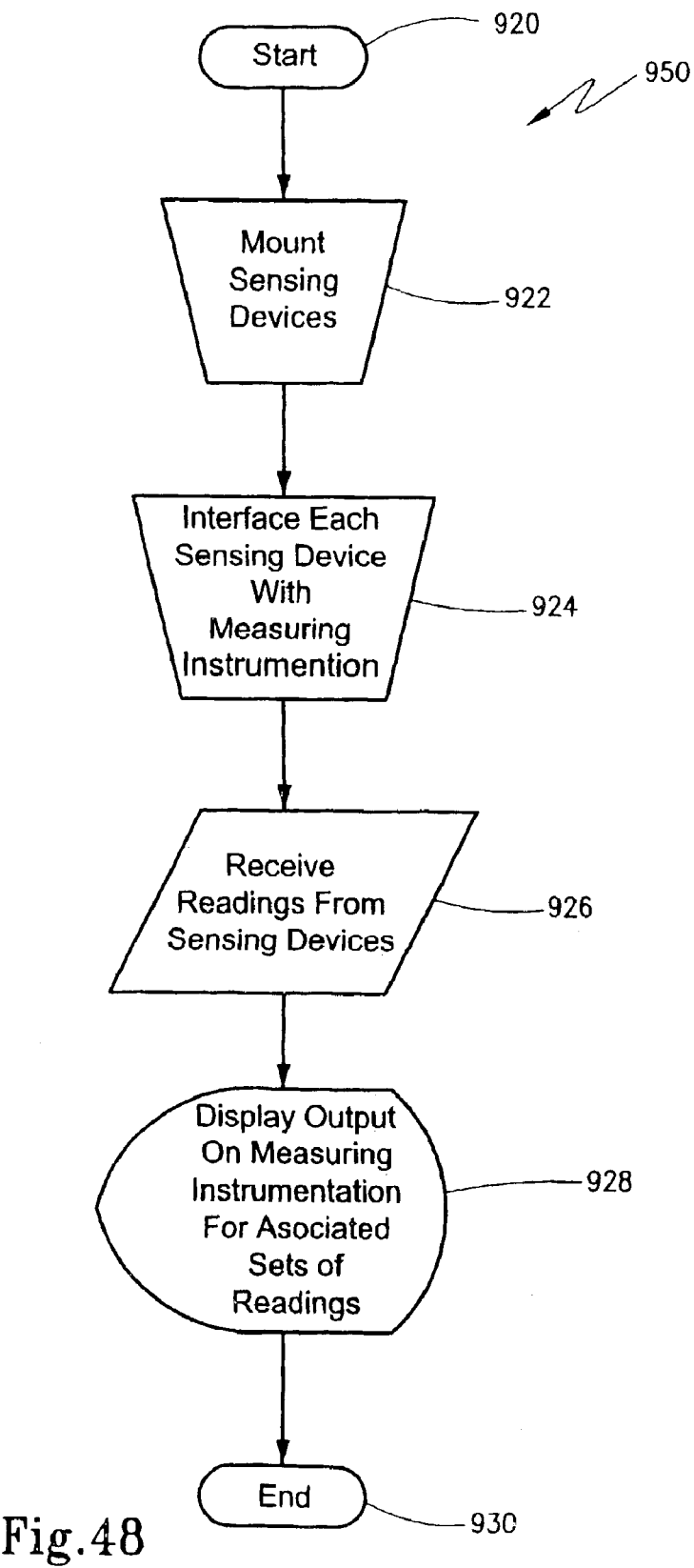
FIG. 48 is a flowchart diagrammatically illustrating the principal concepts associated with a second exemplary embodiment for a methodology according to the present invention.

Swivel body 760 also includes an access port 769 in which is inserted a conventional zerk fitting 780 having a nipple 782. A greaser gun chuck 790 having a cylindrical configuration may then be placed over zerk fitting 780 such that lubrication can be injected into mounting assembly 730 and thus into the access port formed in the machinery. More particularly, as best shown in FIGS. 41 and 42, swivel body 760 has an internal fluid passageway 766 in fluid communication with access port 764 and enlarged hole bore 762. This fluid passageway 766 is machined from an end 761 of swivel body and, thus, a threaded screw plug 784 is inserted into end 761 to prevent fluid leakage. As shown in FIGS. 39 and 40, swivel post 740 has a pair of opposed fluid access ports 747 and 749 which are in fluid communication with an associated fluid passageway 751 formed in the lower portion 746 of swivel post 740.

Accordingly, it can be appreciated that sensing device 720 has the ability to lubricate a bearing while checking the sound characteristics thereof. In doing so, a grease gun is attached to sensing device 720 through chuck 790 and lubrication is injected into swivel body 760 via zerk fitting 780 which is in fluid communication with the access port 764. The fluid then travels within fluid passageway 766 and into fluid passageway 751 of swivel post 740 by virtue of the fluid communication between hole 762 of swivel body 760 and the access ports 747 and 749 of swivel post 740. The lubrication then travels downwardly through the fluid passageway 751 of swivel post 740 and into the bearing for testing. In addition, the pivotability of swivel body 760 about swivel post 740 allows for rotation into a position which is more conveniently accessible by the grease gun or other suitable lubrication source.

An alternative construction for an acoustic sensing device adapted for lubrication of bearings is shown in FIGS. 43–46. Here, sensing device 820 functions similarly to sensing device 720, except that it has a fixed position when mounted. Sensing device 820 again includes sensing device 20 as a component thereof, as well as an adapter 840 and a pair of zerk fittings 850 and 860. Adapter 840 includes a threaded bore 842 sized and adapted to threadedly engage male mounting projection 32 associated with sensing device 20. Adapter 840 also includes a somewhat larger threaded male projection 844 which can be of any of a variety of thread sizes to threadedly engage an appropriately sized threaded bore formed in the bearing to be tested. An access port 846 is formed in adapter 840 which in fluid communication with an internal fluid passageway 848 drilled in adapter 840 and passing through threaded projection 844. Zerk fitting 850 has a projection 852 sized for insertion into access port 846 and an internal fluid cavity (not shown) extending between projection 852 and an opening 854 formed in its bulbous end. Second zerk fitting 860 is constructed the same as zerk fitting 780 discussed above such that its projection 862 is sized for insertion into opening 854. In the embodiment shown, zerk fittings 850 and 860 are connected at an angle of approximately 45° with respect to one another, although the ordinarily skilled artisan would readily appreciate that sensing device 820 could have any desired angled arrangement between the two zerk fittings, such as 90° of otherwise. Accordingly, when lubrication is injected into the mounting assembly 830 of sensing device 820 via the nipple 864 of second zerk fitting 860, it travels through both zerk fittings, into the internal fluid passageway 848 formed in adapter 840 and is then injected into the bearing with sensor 20 operatively used to the detect sound characteristics of the bearing.

From the foregoing it should be appreciated that the present invention also contemplates methodologies for monitoring acoustic emissions from machinery. A first exemplary embodiment of a methodology, as it relates to a single acoustic sensing device, such as any of the ones discussed above, may be appreciated with reference to the flowchart of FIG. 44. Following start at 902, methodology 900 provides at 904 for the mounting of an acoustic sensing device to machinery. At any point in time thereafter, the acoustic sensing device is then coupled with a measuring instrument at 906 and an initial set of detection signals is transmitted to the measuring instrument during a reading interval at 908. This reading interval can be of a selected duration sufficient to obtain characteristic sound detection signals from the acoustic sensing device. Output may then be displayed on the measuring instrument at 910 for the initial set of detection signals. Thereafter, although not necessary, the acoustic sensing device can be decoupled from the measuring instrument at 912 and then later recoupled through the measuring instrument at 914. A subsequent set of detection signals is then obtained and transmitted to the measuring instrument during a subsequent reading interval at 916, after which output is displayed on the measuring instrument for the subsequent set of detection signals at 918. Methodology 900 then ends at 920.

Figure 45:
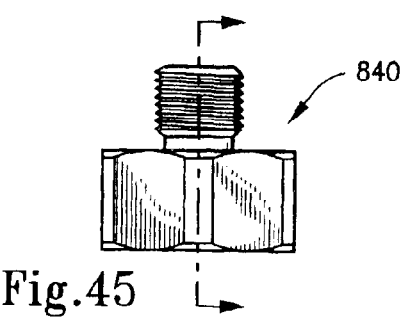
FIG. 45 is a side view in elevation of the adapter used with the acoustic sensing device of FIGS. 43 and 44.
Figure 46:
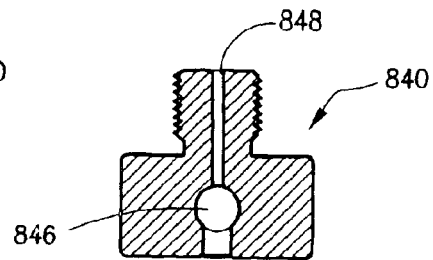
FIG. 46 is a cross-sectional view of the adapter as seen about lines 46—46 in FIG. 45.

A second exemplary embodiment for a methodology according to the present invention, as it relates to multiple sensing devices, can now be appreciated with reference to FIG. 45. Following start at 920, a plurality of sensing devices are mounted to machinery at 922, each in any one of the manners described above. Again, this contemplates that the sensing devices can be of different types or the same. Each sensing device is then interfaced with measuring instrumentation at step 924 and respective sets of readings are received from the sensing devices at 926. Output is then displayed on measuring instrumentation for the associated sets of readings for the sensing devices at 928, after which methodology 950 ends at 930.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

What is claimed is:

1. An acoustic sensing device, comprising:
   (a) a housing assembly having a housing interior including:
      i. a housing body having a first end portion and a second end portion;
      ii. a mount disposed on said first end portion for permitting removable attachment of said housing body relative to a surface mounting region of the machinery, said first end portion of said housing body formed as a substantially planar wall having a substantially planar inner contact surface and a substantially planar outer contact surface that is oriented in a facing relationship to the surface mounting region of the machinery when the housing body is removably attached relative thereto; and
      iii. a coupler disposed on said second end portion for permitting said housing body to be selectively coupled to measuring instrumentation via a communications interface; and
   (b) an acoustic emissions sensor supported within said housing interior in electrical communication with said coupler, said acoustic emissions sensor including a piezoelectric transducer having a mounting face immovably secured to said inner contact surface and extending longitudinally within the housing interior from said mounting face to terminate in an unrestrained free end portion, said piezoelectric transducer operative upon exposure to sound waves propagating through the surface mounting region of the machinery to stress longitudinally within the housing interior and produce corresponding transducer signals, and said acoustic emissions sensor operative, when the housing body is attached relative the surface mounting region and the measuring instrumentation is coupled to said housing body, to produce detection signals from the transducer signals along said communications interface.

2. An acoustic sensing device according to claim 1 wherein said coupler is selected from a group consisting of a coaxial connector, a multi-pin connector and an MIL connector.

3. An acoustic sensing device according to claim 1 wherein said acoustic emissions sensor includes conditioning circuitry in electrical communication with said piezoelectric transducer for receiving said transducer signals and producing said detection signals.

4. An acoustic sensing device according to claim 3 wherein said conditioning circuitry is contained on a common circuit board disposed with said housing interior.

5. An acoustic sensing device according to claim 4 including a retainer which immovably supports said circuit board within the housing interior.

6. An acoustic sensing device according to claim 1 wherein said acoustic emissions sensor includes conditioning circuitry for receiving said transducer signals and for producing said detection signals.

7. An acoustic sensing device according to claim 1 wherein said mount is formed integrally with said housing body and projects from the first end portion thereof.

8. An acoustic sensing device according to claim 7 wherein said housing body includes a main body section that includes said mount and an end cap secured to said main body section.

9. An acoustic sensing device according to claim 8 including a plurality of fastening elements for securing said end cap to said main body section.

10. An acoustic sensing device according to claim 8 wherein each of said main body section and said end cap is formed from an electrically conductive material.

11. An acoustic sensing device according to claim 8 wherein said main body section is formed from an electrically conductive material and said end cap is formed from an electrically conductive material having an insulative coating, and including an electrically conductive compression spring interposed between facing portions of said main body section and said end cap.

12. An acoustic sensing device according to claim 1 including a mounting adapter for removably attaching said housing body relative to the surface mounting region of the machinery.

13. An acoustic sensing device according to claim 12 wherein said mount includes a threaded projection of a selected thread size which extends from the first end portion of said housing body, and wherein said mounting adapter has a correspondingly sized first threaded bore formed therein for matably receiving said threaded projection.

14. An acoustic sensing device according to claim 13 wherein said mounting adapter has a second threaded bore for threadedly engaging a correspondingly sized threaded tapping screw projecting from the surface mounting region of the machinery.

15. An acoustic sensing device according to claim 13 wherein said mounting adapter includes an associated threaded projection of a selected thread size which is adapted to threadedly engage a correspondingly sized threaded bore formed in the surface mounting region of the machinery.

16. An acoustic sensing device according to any of claims 12 and 13 wherein said mounting adapter includes a set of magnetic elements for magnetically coupling said mounting adapter to the surface mounting region of the machinery.

* * * * *